United States Patent
Lee et al.

(10) Patent No.: US 9,839,409 B2
(45) Date of Patent: Dec. 12, 2017

(54) IMAGE DISPLAY SYSTEM AND METHOD OF FITTING MULTIPLE MODELS TO IMAGE

(71) Applicant: SAMSUNG MEDISON CO., LTD., Hongcheon-gun (KR)

(72) Inventors: Kwang-hee Lee, Hongcheon-gun (KR); Jae-moon Jo, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 328 days.

(21) Appl. No.: 14/550,454

(22) Filed: Nov. 21, 2014

(65) Prior Publication Data

US 2015/0138245 A1    May 21, 2015

Related U.S. Application Data

(60) Provisional application No. 61/907,269, filed on Nov. 21, 2013.

(30) Foreign Application Priority Data

Oct. 31, 2014    (KR) .................. 10-2014-0150636

(51) Int. Cl.
*A61B 8/00* (2006.01)
*G06T 7/11* (2017.01)
(Continued)

(52) U.S. Cl.
CPC .............. *A61B 8/44* (2013.01); *G06K 9/6277* (2013.01); *G06T 7/11* (2017.01); *G06T 7/143* (2017.01);
(Continued)

(58) Field of Classification Search
CPC ................... A61B 8/44; G06T 7/0081; G06T 2207/10132; G06T 2207/30021; G06T 7/0087; G06K 9/6277
See application file for complete search history.

(56) References Cited

U.S. PATENT DOCUMENTS

| 7,251,356 B2 | 7/2007 | Seo et al. |
| 8,705,876 B2 | 4/2014 | Vaddadi et al. |

(Continued)

FOREIGN PATENT DOCUMENTS

| KR | 10-0526817 B1 | 11/2005 |
| KR | 10-0944293 B1 | 2/2010 |
| KR | 10-2012-0099111 A | 9/2012 |

OTHER PUBLICATIONS

Zheng, Deterministically Maximizing Feasible Subsystem for Robust Model Fitting with Unit Norm Constraint, Computer Vision and Pattern Recognition (CVPR), 2011 IEEE Conference, Jun. 2011, pp. 1825-1832.*

(Continued)

*Primary Examiner* — Mark Zimmerman
*Assistant Examiner* — Phuc Doan
(74) *Attorney, Agent, or Firm* — Sughrue Mion, PLLC

(57) ABSTRACT

Provided is an image processing apparatus for fitting a model to image data. The image processing apparatus determines a final parameter set and a final inlier scale of a first model by iteratively performing a model estimation process and an inlier scale estimation process, wherein the model estimation process determines a model parameter set, and the inlier scale estimation process determines an inlier scale by using the determined model parameter set.

13 Claims, 23 Drawing Sheets
(19 of 23 Drawing Sheet(s) Filed in Color)

(51) Int. Cl.
*G06T 7/143* (2017.01)
*G06K 9/62* (2006.01)
(52) U.S. Cl.
CPC ............... *G06T 2207/10132* (2013.01); *G06T 2207/30021* (2013.01)

(56) References Cited

U.S. PATENT DOCUMENTS

| | | |
|---|---|---|
| 2010/0092026 A1* | 4/2010 | Fan ...................... G06K 9/4609 382/100 |
| 2012/0224760 A1 | 9/2012 | Goshen et al. |
| 2013/0202175 A1 | 8/2013 | Lee |

OTHER PUBLICATIONS

Vincent, Detecting planar homographies in an image pair, ISPA 2001, pp. 182-187.*

Wong, A preference analysis approach to robust geometric model fitting in computer vision, 2013, The University of Adelaide, pp. 19-20.*

* cited by examiner

IMAGE DISPLAY SYSTEM AND METHOD OF FITTING MULTIPLE MODELS TO IMAGE

RELATED APPLICATIONS

This application claims the benefit of U.S. Provisional Application No. 61/907,269, filed on Nov. 21, 2013, in the US Patent and Trade Office and Korean Patent Application No. 10-2014-0150636, filed on Oct. 31, 2014, in the Korean Intellectual Property Office, the disclosures of which are incorporated herein in their entireties by reference.

BACKGROUND

1. Field

One or more exemplary embodiments relate to an image display system and method of fitting multiple models to image data, and more particularly, to an image display system and method of fitting multiple models to an image more accurately.

2. Description of the Related Art

Among various types of image diagnosis devices, an ultrasound diagnosis device transmits ultrasound signals generated by transducers of a probe to an object and receives echo signals reflected from the object, thereby obtaining images of the interior of the object. In particular, an ultrasound diagnosis device may be used for various medical purposes such as observation of the inside of an object, detection of foreign substances, and assessment of injuries. Such an ultrasound diagnosis device may provide highly stable performance and display information regarding an object in real-time compared to an X-ray diagnosis apparatus. Furthermore, there is no risk of radioactivity exposure using an ultrasound diagnosis apparatus, unlike in the use of an X-ray diagnosis apparatus, and thus, the ultrasound diagnosis apparatus is very safe. Therefore, an ultrasound diagnosis apparatus is widely used together with other types of imaging diagnosis devices.

Such an ultrasound diagnosis apparatus, a computed tomography (CT) apparatus, an X-ray apparatus, and a magnetic resonance imaging (MRI) apparatus may perform imaging of an object to acquire a two-dimensional (2D) or three-dimensional (3D) image. A user needs to fit a specific model to the acquired 2D or 3D image for observation, and various algorithms for fitting an accurate model are being presented. However, due to inherent limitations of the algorithms, it may often be difficult to acquire a model that is accurately fit to an image.

SUMMARY

One or more exemplary embodiments include an image display system and method of fitting multiple models to an image more accurately.

Additional aspects will be set forth in part in the description which follows and, in part, will be apparent from the description, or may be learned by practice of the presented exemplary embodiments.

According to one or more exemplary embodiments, an image processing apparatus includes: a storage configured for storing image data comprising data of a first model; and a processor configured for determining a final model parameter set and a final inlier scale of the first model by iteratively performing a model estimation process and an inlier scale estimation process, wherein the model estimation process determines a model parameter set from the image data by using an initial inlier scale, and the inlier scale estimation process determines an inlier scale by using the model parameter set. When the model estimation process is repeated, in the repeated model estimation process, a new model parameter set is determined by using an inlier scale determined according to an immediately previously performed inlier scale estimation process, and in the inlier scale estimation process, a new inlier scale is determined using a model parameter set determined according to an immediately previously performed model estimation process.

Model parameter sets and inlier scales determined by iteratively performing the model estimation process and the inlier scale estimation process may converge to the final model parameter set and the final inlier scale of the first model, respectively.

The image data may include data of multiple models including the first model and a second model. The processor may be further configured for performing an inlier removal process whereby first inlier data located within the final inlier scale of the first model is removed from the image data based on the final model parameter set and the final inlier scale of the first model, and performing a final determination process whereby a final model parameter set and a final inlier scale of the second model are determined by iteratively performing the model estimation process and the inlier scale estimation process on the image data from which the first inlier data has been removed.

The processor may determine final model parameter sets and final inlier scales of all of the multiple models by iteratively performing, each time a final model parameter set and a final inlier scale of one of the multiple models are determined, the inlier removal process and the final determination process on another one of the multiple models.

The first inlier scale may be set by a user input.

The model estimation process may be performed using Maximum Feasible Subsystem (MaxFS) as a deterministic method.

The inlier scale estimation process may be performed using at least one method from among Iterative Kth Ordered Scale Estimator (IKOSE), Median (MED), Median Absolute Deviation (MAD), and KOSE.

The image data may include an ultrasound image, and the first model may be a geometric shape, and be one of a straight line, a circle, an ellipse, a plane, a sphere, and a curved surface.

The first model may be a linear or non-linear model that is estimated from the image data and is at least one from among homography estimation, fundamental matrix estimation, optical flow estimation, and motion estimation.

According to one or more exemplary embodiments, an image processing method includes: iteratively performing a model estimation process and an inlier scale estimation process on image data including data of a first model, wherein the model estimation process determines a model parameter set from the image data by using an initial inlier scale, and the inlier scale estimation process determines an inlier scale by using the model parameter set, and determining a final model parameter set and a final inlier scale of the first model based on a result obtained by the iteratively performing of the model estimation process and the inlier scale estimation process, wherein when the model estimation process is repeated, in the repeated model estimation process, a new model parameter set is determined by using an inlier scale determined according to an immediately previously performed inlier scale estimation process. In the inlier scale estimation process, a new inlier scale is determined using a model parameter set determined according to an immediately previously performed model estimation process.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of the exemplary embodiments, taken in conjunction with the accompanying drawings in which.

DETAILED DESCRIPTION

Figure 1:
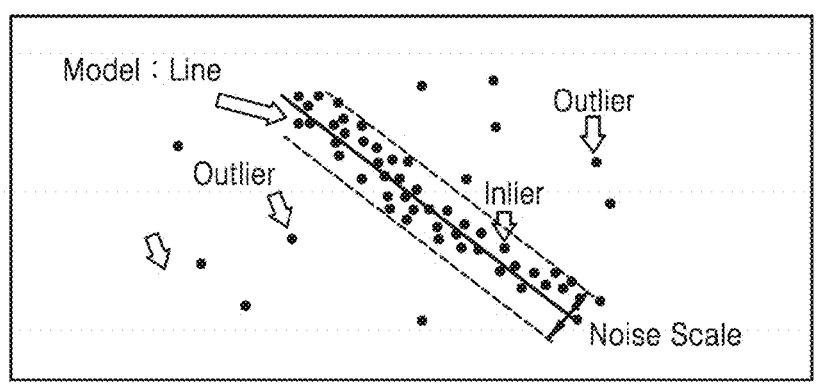
FIG. 1 illustrates an example of fitting a line as a model to image data including a plurality of points.

Reference will now be made in detail to exemplary embodiments, examples of which are illustrated in the accompanying drawings, wherein like reference numerals refer to like structural elements throughout. Expressions such as "at least one of," when preceding a list of elements, modify the entire list of elements and do not modify the individual elements of the list.

The terms used in this specification are those general terms currently widely used in the art in consideration of functions in regard to exemplary embodiments, but the terms may vary according to the intention of those of ordinary skill in the art, precedents, or emergence of a new technology in the art. Also, specified terms may be selected by the applicant, and in this case, the detailed meaning thereof will be described in the detailed description of the inventive concept. Thus, the terms used in the specification should be understood not as simple names but based on the meaning of the terms and the overall description of the inventive concept.

Throughout the specification, it will also be understood that when a component "includes" or "comprises" an element, unless there is a particular description contrary thereto, it should be understood that the component can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object obtained using an ultrasound wave. Furthermore, in the present specification, an "object" may include a person or an animal, or a part of a person or an animal. For example, the object may include organs such as the liver, the heart, the womb, the brain, a breast, and the abdomen, or a blood vessel. Furthermore, the "object" may include a phantom. The phantom is a material having a volume that is approximately close to the density and effective atomic number of a living organism.

In the present specification, a "user" refers to a medical professional, such as a doctor, a nurse, a medical laboratory technologist, and a medical imaging expert, and a technician who repairs a medical apparatus, but the user is not limited thereto.

FIG. 1 illustrates an example of fitting a line as a model in image data including a plurality of points.

The image data may include a plurality of points, most of which are arranged from top left to bottom right. In view of a distribution of the points, a user may fit a specific model, e.g., a line, which is oriented from the top left to the bottom edge, to image data. The line which is fitted to the image data may be a straight line. In this case, the model may be a geometric shape, and fitting of a geometric shape may include determining a parameter set that may be used to define the geometric shape. For example, fitting of the line shown in FIG. 1 may be performed by determining a parameter set for the line, e.g., coordinates or positions of two points that define the line.

Furthermore, the plurality of points in the image data are classified into inliers and outliers with respect to the line determined as a model. For example, the inliers may be points located close to the line while the outliers may be points located far away from the line. Alternatively, points that are located within and outside a predetermined distance may be classified as inliers and outliers, respectively. In this case, the predetermined distance used to identify the inliers and outliers is referred to as an inlier scale or noise scale.

Figure 2:
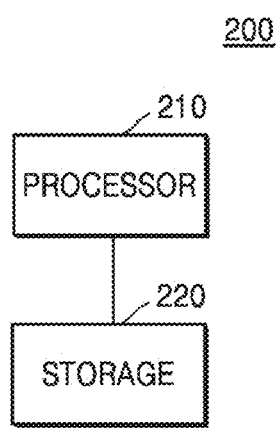
FIG. 2 is a diagram of an image processing apparatus according to an exemplary embodiment.

FIG. 2 illustrates an image processing apparatus 200 according to an exemplary embodiment. Referring to FIG. 2, the image processing apparatus 200 according to the present exemplary embodiment includes a storage 220 and a processor 210.

The storage 220 stores image data. The image data may be acquired by medical equipment such as an ultrasound system, a computed tomography (CT) apparatus, a medical resonance imaging (MRI) apparatus, or an X-ray apparatus. The image data may be two-dimensional (2D) or three-dimensional (3D) data.

Furthermore, the image data may be acquired by the image processing apparatus 200 or received by the image processing apparatus 200 from an external device.

The image data may include data of one or more models. A model may be a straight line, a circle, an ellipse, a plane, a sphere, a curved surface or other geometric shapes. Alternatively, the model may be a linear or non-linear model that can be estimated from the image data. For example, the model may be estimated using a homography estimation method, a fundamental matrix estimation method, an optical flow estimation method, or a motion estimation method.

The processor 210 may determine a model included in image data by performing image processing on the image data. In one exemplary embodiment, the processor 210 may determine the model by determining a set of parameters thereof. For example, if a line is included in the image data as a model, the processor 210 may determine the line by determining coordinates or positions of two points that may define the line. As another example, if a circle is included in the image data as a model, the processor 210 may determine coordinates or positions of a central point or a radius that may define the circle.

According to one exemplary embodiment, the processor 210 determines a set of parameters of a model by using a predetermined initial inlier scale and then determines a new inlier scale by using the determined set of parameters. Subsequently, the processor 210 determines a new set of parameters by using the new inlier scale. If a process of determining a set of parameters of a model by using an inlier scale is referred to as a model estimation process and a process of determining an inlier scale by using parameters of a model is referred to as an inlier scale estimation process, the processor 210 may determine parameters and a inlier scale more accurately by iteratively performing the model estimation process and the inlier scale estimation process in a sequential manner. The above-described processes according to exemplary embodiments are called an Iterative Maximum Feasible Subsystem Framework (IMaxFS) algorithm.

In one exemplary embodiment, to start the sequential iteration of a model estimation process and an inlier scale estimation process, an initial inlier scale is given at the beginning of the iteration, and a model estimation process may be performed first by using the initial inlier scale. According to exemplary embodiments, the initial inlier scale may be set to a value that is sufficiently small so as to determine a model parameter, so that an initial model parameter is not biased. Setting of an initial inlier scale will be described in more detail below.

Furthermore, according to exemplary embodiments, in a model estimation process, when an inlier scale is known, parameters of a model may be determined using an algorithm such as MaxFS or Random Sample Consensus (RANSAC). According to exemplary embodiments, in an inlier scale estimation process, when parameters of a model are given, an inlier scale of a model may be determined by using an algorithm such as Iterative Kth Ordered Scale Estimator (IKOSE).

An IMaxFS algorithm may be performed in the following way. First, as described above, the IMaxFS algorithm alternately estimates an inlier scale S and model parameters. When the inlier scale S is known, the model parameters are estimated using MaxFS, and a current inlier scale is estimated from the estimated model parameters by performing an IKOSE algorithm. According to the IKOSE algorithm that assumes that inliers have a Gaussian distribution. If a model parameter deviates from a true model or the Kth ordered absolute residual for the IKOSE algorithm belongs to an outlier, the determined inlier scale may be either biased or even break down. To avoid such a bias or breakdown, in the IKOSE algorithm, K is fixed at 10% of the entire image data. Furthermore, to prevent an initially determined model parameter from being badly biased against a true model, an initial inlier scale is set to a very small value and gradually increases until the number of inliers determined by using MaxFS is greater than a particular threshold.

Figure 3:
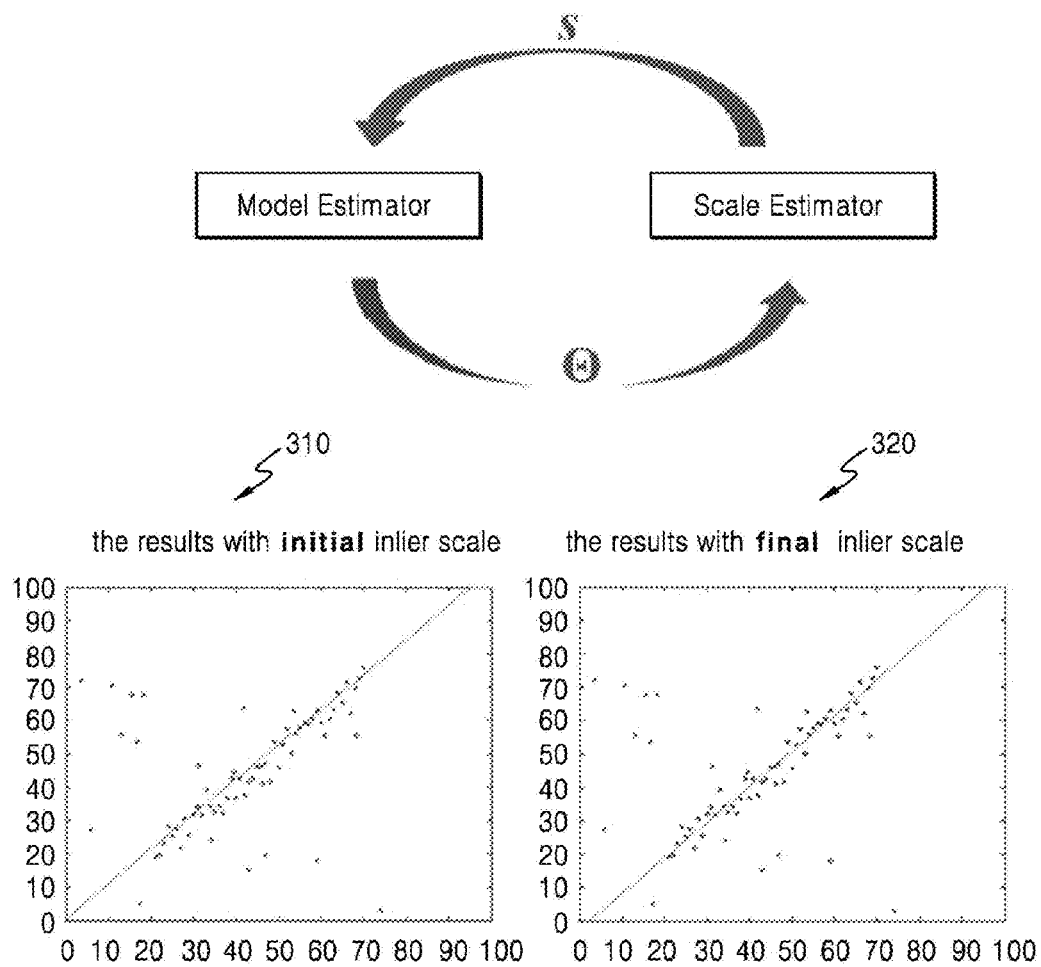
FIG. 3 is a diagram illustrating a process of fitting a model to image data according to an exemplary embodiment.

FIG. 3 is a diagram illustrating a process of fitting a model to image data according to an exemplary embodiment.

Referring to FIG. 3, as described above, according to an exemplary embodiment, a model estimation process using an inlier scale S and an inlier scale estimation process using parameters θ determined via the model estimation process are performed in an iterative manner. A data distribution 310 represents an initial result obtained when an initial inlier scale is set to a very small value and a model estimation process according to an exemplary embodiment is performed using the initial inlier scale. A data distribution 320 represents a final result obtained when a model estimation process and an inlier scale estimation process are performed iteratively according to an exemplary embodiment.

In addition, according to an exemplary embodiment, if image data includes multiple models, e.g., first and second models, the first and second models may be sequentially fitted to the image data. In this case, the image processing apparatus 200 in FIG. 2 first determines parameters and inliers of the first model by using the IMaxFS algorithm described above, followed by removal of the inliers of the first model from the image data. Then, the second model may then be fitted to the remaining image data by applying an IMaxFS algorithm again thereto. By iterating this process, parameters and inliers of each of the plurality of models may be determined.

Figure 4:
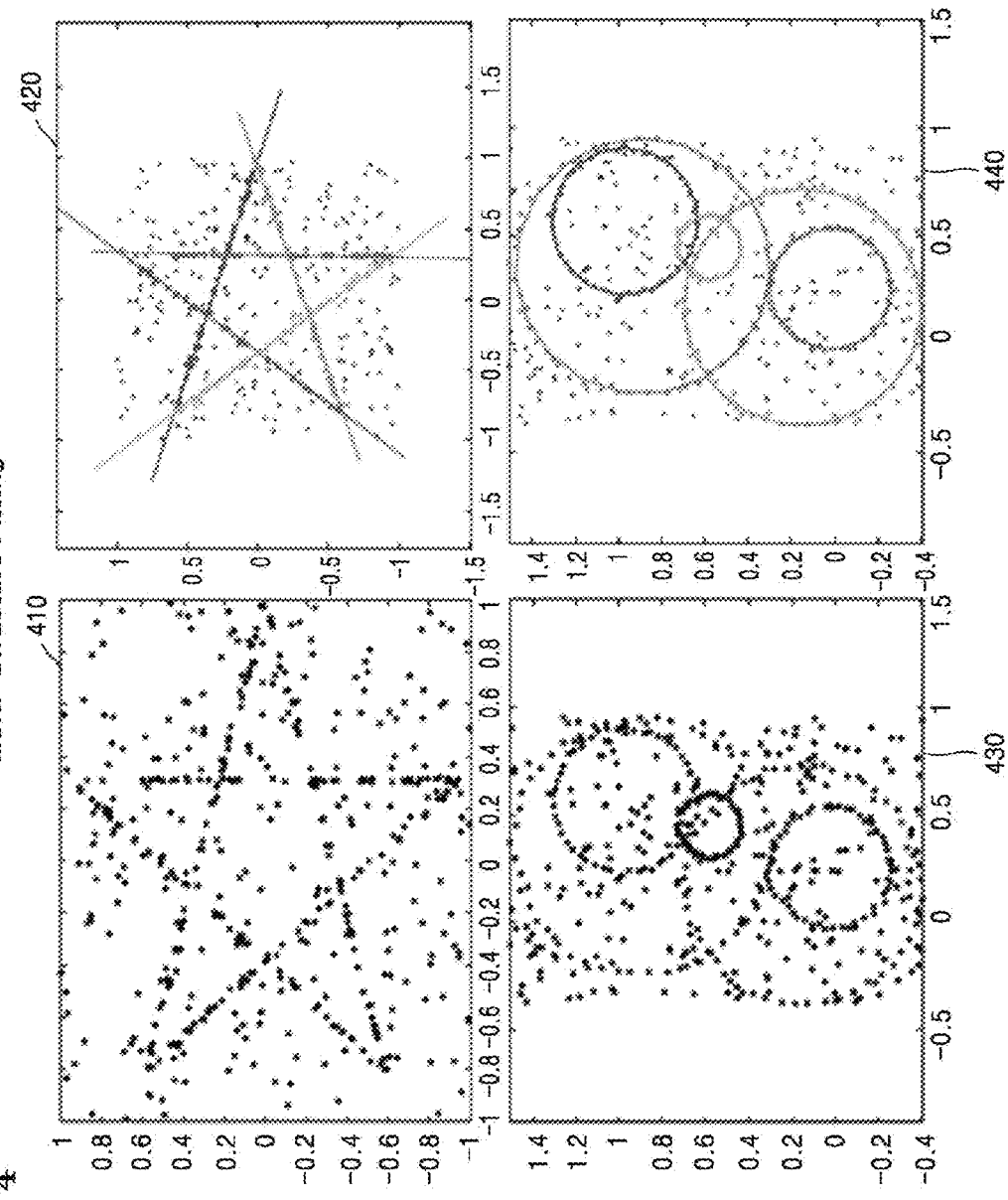
FIG. 4 illustrate examples of fitting multiple models to image data according to an exemplary embodiment.

FIG. 4 illustrates examples of fitting multiple models to image data 410, 420, and 430 according to an exemplary embodiment.

Referring to FIG. 4, image data 410 includes a plurality of straight line models. By iteratively applying an IMaxFS algorithm according to an exemplary embodiment, five straight line models may be acquired accurately as shown in image data 420. Similarly, image data 430 include a plurality of circle models. By iteratively applying the IMaxFS algorithm to the plurality of circle models, five circle models may be acquired accurately as shown in image data 440.

Figure 5:
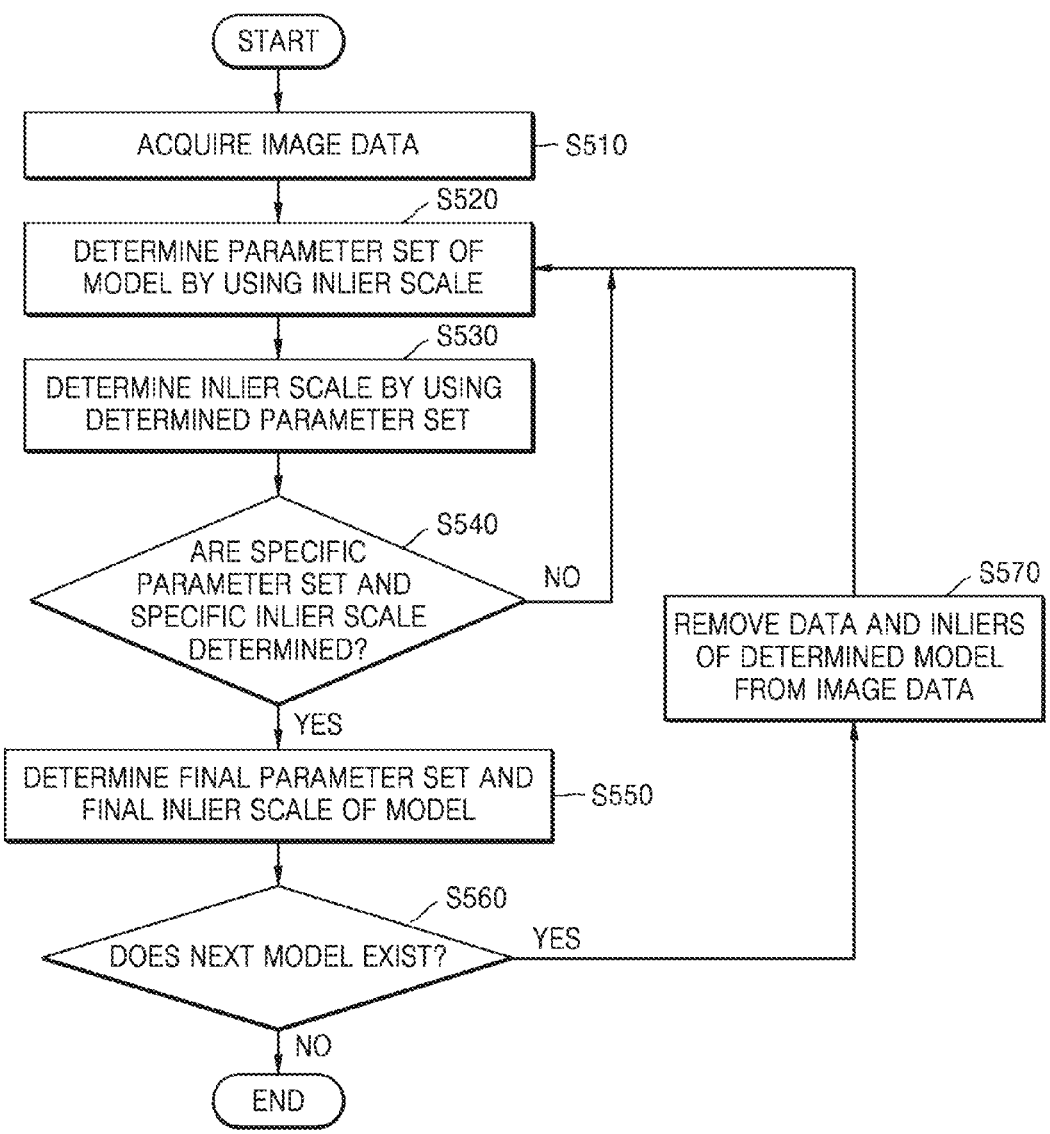
FIG. 5 is a flowchart of a method of fitting multiple models to image data according to an exemplary embodiment.

FIG. 5 is a flowchart of a method of fitting multiple models to image data according to an exemplary embodiment.

Referring to FIG. 5, an image processing apparatus acquires image data including multiple models (S510).

The image processing apparatus determines a parameter set of a first model by performing a model estimation process on the first model based on an inlier scale (S520). When operation S520 is initially performed, an initial inlier scale may be preset or received as a user input.

The image processing apparatus may determine a new inlier scale by performing an inlier scale estimation process based on the determined parameter set (S530).

The image processing apparatus determines whether the determined parameter set and the new inlier scale converges to a specific parameter set and a specific inlier scale (S540). If the specific parameter set and the specific inlier scale are not yet determined, the image processing apparatus may determine a parameter set again by performing operation S520 based on the immediately previously determined inlier scale, and then determine a new inlier scale again by performing operation S530. In this way, operations S520, S530, and S540 are repeated until that parameter sets and inlier scales determined according to iteratively performed the model estimation processes (S520) and the inlier scale estimation processes (S530), respectively are determined to converge to a specific parameter set and a specific inlier scale, respectively.

If the immediately previously determined parameter set and inlier scale converge to a specific parameter set and a specific inlier scale, respectively, the image processing apparatus performs operation S550.

The image processing apparatus determines the specific parameter set and the specific inlier scale as a final parameter set and a final inlier scale of the first model, respectively (S550).

Subsequently, the image processing apparatus determines whether a next model other than the first model is present in the image data (S560). If the next model is not present in the image data, the image processing apparatus terminates the model fitting process according to the present exemplary embodiment.

If the image data further include a model other than the first model, i.e., the next model is present in the image data in operation S560, the image processing apparatus performs operation S570.

The image processing apparatus removes data and inliers of the immediately previously determined model, which is the first model from the image data (S570).

Then, the image processing apparatus performs a process of determining a parameter set and an inlier scale on the next model through operations S520, S530, and S540.

Through the processes, the image processing apparatus may determine a parameter set and an inlier scale for each of the multiple models in the image data.

Figure 6A:
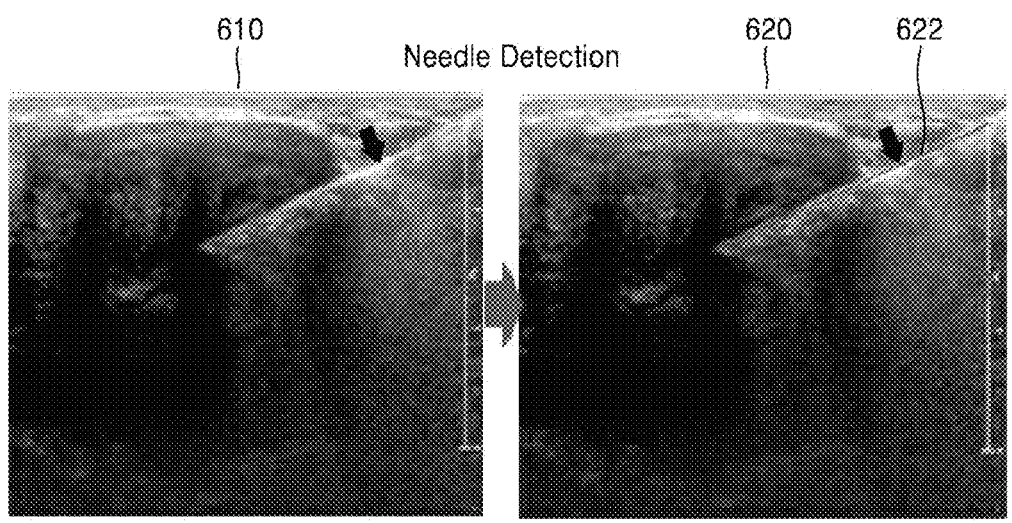
FIGS. 6A and 6B illustrate examples where a method of fitting multiple models to image data according to an exemplary embodiment is applied to an ultrasound mage.
Figure 6B:
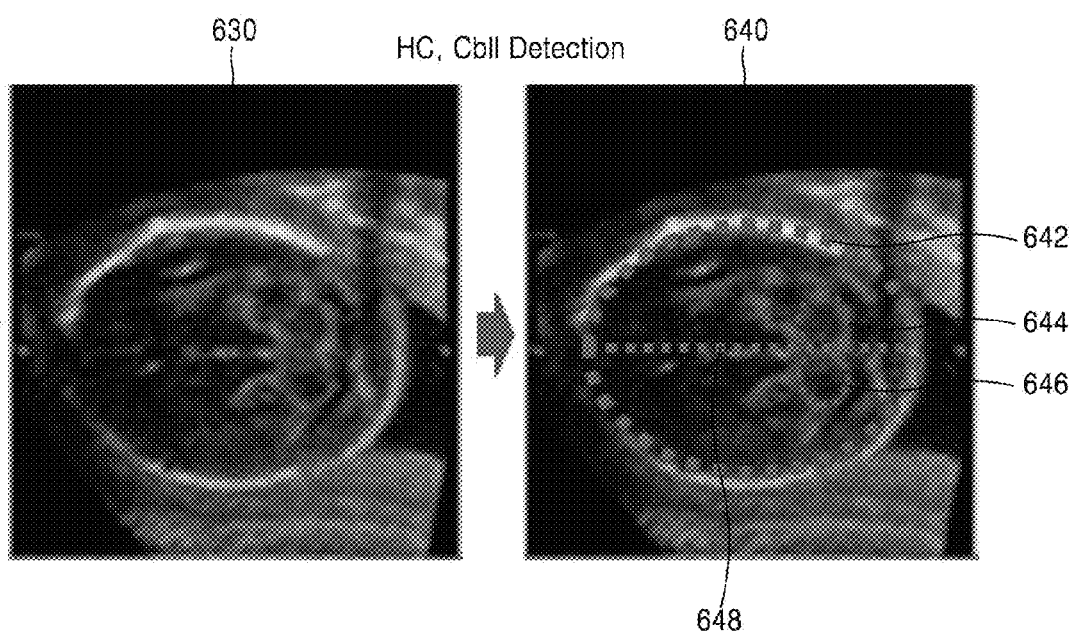

FIGS. 6A and 6B illustrate examples where a method of fitting multiple models to image data according to an exemplary embodiment is applied to an ultrasound mage.

Referring to FIG. 6A, image data includes ultrasound data. The image processing apparatus 200 in FIG. 2 generates an ultrasound image 610 from ultrasound data. The image processing apparatus also determines a model included in the ultrasound data by applying a model estimation process according to an exemplary embodiment. In detail, the image processing apparatus determines a line 622 from the ultrasound image 610 by using an IMaxFS algorithm according to an exemplary embodiment. In actual applications, when the shape of a needle used for ultrasound scanning is included in the ultrasound image 610, a position of the needle may be identified via a model estimation process according to an exemplary embodiment.

Figure 7:
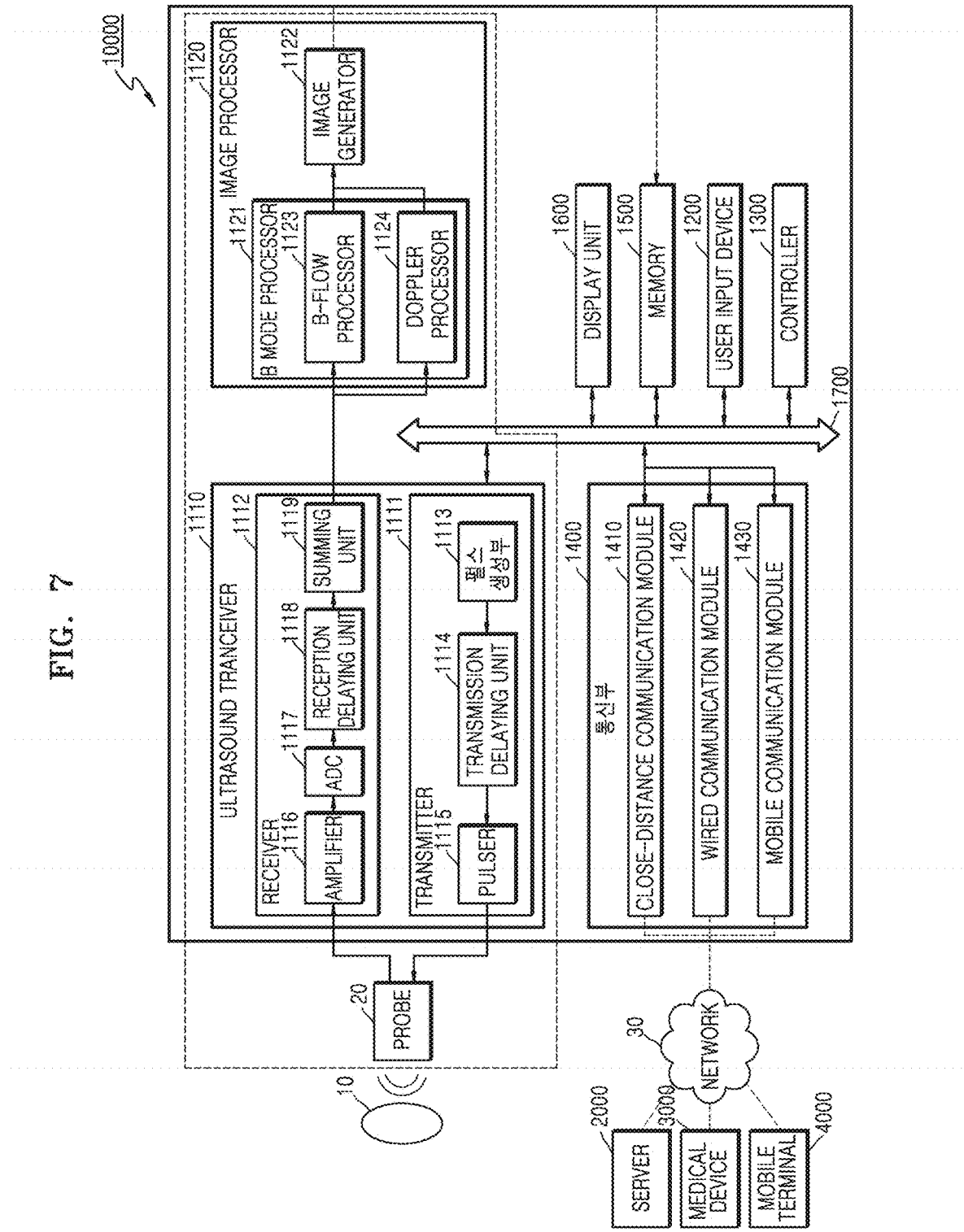
FIG. 7 is a block diagram of a configuration of an ultrasound diagnosis apparatus to which an image processing apparatus according to an exemplary embodiment may be applied.

Referring to FIG. 6B, the image data includes ultrasound data. The image processing apparatus generates an ultrasound image 630 from the image data. The image processing apparatus also determines a model included in the ultrasound data by using a model estimation process according to an exemplary embodiment. The ultrasound data includes multiple models. According to an exemplary embodiment, the image processing apparatus determines one ellipse 642, two circles 644 and 646, and one straight line 648 by applying an IMaxFS algorithm. In a practical application, since the ultrasound image 630 of a skull has an elliptical shape, the ellipse 642 is fit to the ultrasound image 630 of the skull, and coordinates of the fit ellipse 642 may be used for medical diagnosis of an object FIG. 7 is a block diagram of an ultrasound diagnosis apparatus 10000 to which the image processing apparatus 200 according to an exemplary embodiment may be applied. Referring to FIG. 7, the ultrasound diagnosis apparatus 10000 may include a probe 20, an ultrasound transceiver 1110, an image processor 1120, a communication unit 1400, a display unit 1600, a memory 1500, a user input device 1200, and a controller 1300, which may be connected to one another via buses 1700.

A method of editing an ultrasound image, according to an exemplary embodiment, may be performed by the ultrasound diagnosis apparatus 10000 of FIG. 7, and the image processing apparatus 200 according to an exemplary embodiment may be included in the ultrasound diagnosis apparatus 10000 of FIG. 7.

The image processing apparatus 200 of FIG. 2 may perform some or all functions performed by the ultrasound diagnosis apparatus 10000 of FIG. 7. The processor 210 of FIG. 2 may include some or perform some functions of the ultrasound transceiver 1110, the image processor 1120, the communication unit 1400, and the controller 1300 of FIG. 7. The storage 220 of FIG. 2 may correspond to the memory 1500 of FIG. 7.

The components of the ultrasound diagnosis apparatus 10000 of FIG. 7 will be described below.

An ultrasound image data acquiring unit 1100 according to an exemplary embodiment may obtain ultrasound image data of an object 10. The ultrasound image data according to an exemplary embodiment may be 2D ultrasound image data or 3D ultrasound image data of the object 10.

According to an exemplary embodiment, the ultrasound image data acquiring unit 1100 may include the probe 20, the ultrasound transceiver 1110, and the image processor 1120.

The probe 20 transmits ultrasound signals to the object 10 according to a driving signal applied by the ultrasound transceiver 1110 and receives ultrasound echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 10000 by wire or wirelessly. According to the embodiments of the present inventive concept, the ultrasound diagnosis apparatus 10000 may include a plurality of probes 20. According to an exemplary embodiment, the probe 20 may include at least one selected from a 1-dimensional (1D) probe, a 1.5-dimensional probe, a 2D (matrix) probe, and a 3D probe.

A transmitter 1111 supplies a driving signal to the probe 20. The transmitter 1111 includes a pulse generator 1113, a transmission delaying unit 1114, and a pulser 1115. The pulse generator 1113 generates pulses for forming transmission ultrasound waves based on a predetermined pulse repetition frequency (PRF), and the transmission delaying unit 1114 delays the pulses by delay times necessary for determining transmission directionality. The pulses, which have been delayed, correspond to a plurality of piezoelectric vibrators included in the probe 20, respectively. The pulser 1115 applies a driving signal (or a driving pulse) to the probe 20 based on timing corresponding to each of the pulses, which have been delayed.

A receiver 1112 generates ultrasound data by processing echo signals received from the probe 20. The receiver 1112 may include an amplifier 1116, an analog-to-digital converter (ADC) 1117, a reception delaying unit 1118, and a summing unit 1119. The amplifier 1116 amplifies echo signals in each channel, and the ADC 1117 performs analog-to-digital conversion on the each of the amplified signals. The reception delaying unit 1118 delays digital echo signals output by the ADC 1117 by delay times necessary for determining reception directionality, and the summing unit 1119 generates ultrasound data by summing the echo signals processed by the reception delaying unit 1118. For example, the summing unit 1119 may generate shoulder ultrasound image data. Alternatively, the summing unit 1119 may obtain shoulder ultrasound image data in real-time while a drug is injected into a bursa through a needle.

The image processor 1120 generates an ultrasound image by scan-converting ultrasound image data generated by the ultrasound transceiver 1110. The ultrasound image may be not only a grayscale ultrasound image obtained by scanning an object in an amplitude (A) mode, a brightness (B) mode, and a motion (M) mode, but also a Doppler image showing movements of an object via a Doppler effect. The Doppler image may be a blood flow Doppler image showing flow of blood (also referred to as a color Doppler image), a tissue Doppler image showing movements of tissue, or a spectral Doppler image showing a moving speed of an object as a waveform.

A B mode processor 1123 extracts B mode components from ultrasound image data and processes the B mode components. An image generator 1122 may generate a B mode image indicating signal intensities as brightness based on the B mode components extracted by the B mode processor 1123. For example, the image generator 1122 may generate a shoulder ultrasound image, including a deltoid, fat layers, bursae, and tendons, as a 2D B mode image.

The image generator 1122 may sequentially generate a plurality of B mode images. For example, the image generator 1122 may generate a first B mode image and a second B mode image. Alternatively, the image generator 1122 may generate a shoulder ultrasound image in real-time while a drug is injected into a bursa through a needle.

A Doppler processor 1124 may extract Doppler components from ultrasound image data, and the image generator 1122 may generate a Doppler image indicating movements of an object as colors or waveforms based on the extracted Doppler components.

According to an exemplary embodiment, the image generator 1122 may generate a 3D ultrasound image via volume-rendering with respect to volume data and may also generate an elasticity image by imaging the deformation of the object 10 due to pressure. Furthermore, the image generator 1122 may generate a speckle detection image by estimating moving paths of speckles from the ultrasound image data and indicating movements of the speckles as arrows or colors based on the estimated moving paths.

Furthermore, the image generator 1122 may display various pieces of additional information on an ultrasound image by using text and graphics. For example, the image generator 1122 may add at least one annotation related to all or some portions of the ultrasound image to the ultrasound image. That is, the image generator 1122 may analyze the ultrasound image and recommend at least one annotation related to all or some portions of the ultrasound image based on the analysis result. Alternatively, the image generator 1122 may add at least one annotation selected by the user to the ultrasound image.

The image processor 1120 may extract an interest region from the ultrasound image by using an image processing algorithm. In this case, the image processor 1120 may add colors, patterns, or boundaries to the interest region.

The user input device 1200 is a unit via which a user (for example, a sonographer) inputs data for controlling the ultrasound diagnosis apparatus 10000. For example, the user input device 1200 may include a keypad, a dome switch, a touchpad (a capacitive overlay type, a resistive overlay type, an infrared beam type, an integral strain gauge type, a surface acoustic wave type, a piezoelectric type, etc.), a trackball, and a jog switch. However, exemplary embodiments of the present inventive concept are not limited thereto, and the user input device 1200 may further include any one of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

According to an exemplary embodiment, the user input device 1200 may detect not only a real-touch but also a proximity touch. The user input device 1200 may detect a touch input (for example, touch and holding, tapping, double tapping, or flicking) on an ultrasound image. Also, the user input device 1200 may detect a drag input from a point where a touch input is detected. The user input device 1200 may detect a multi-touch input (for example, pinching) on at least two points in the ultrasound image.

According to an exemplary embodiment, the user input device 1200 may receive an input for selecting an interest region in a B mode image. For example, the user input device 1200 may receive a user input for selecting an interest region, including a deltoid and tendons, in a shoulder ultrasound image.

The controller 1300 may control all operations of the ultrasound diagnosis apparatus 10000. For example, the controller 1300 may control operations of the ultrasound image data acquiring unit 1100, the user input device 1200, the communication unit 1400, a memory 1500, and the display unit 1600.

The controller 1300 may detect a fat layer located between a deltoid and tendons based on echo signal intensity information included in shoulder ultrasound image data.

For example, the controller 1300 may detect a region of which intensities of echo signals are greater than a threshold value as a fat layer. Also, in the shoulder ultrasound image, the controller 1300 may determine a first boundary of which the degree of change in intensity of echo signals is greater than a positive first threshold value as an upper portion of the fat layer and a second boundary of which the degree of change in intensity of echo signals is less than a negative second threshold value as a lower portion of the fat layer. Also, the controller 1300 may detect a thickness of the fat layer based on a distance between the first and second boundaries.

The controller 1300 may detect a bursa located between the fat layer and the tendons by using a location of the fat layer. For example, the controller 1300 may determine an anechoic zone under the fat layer as the bursa.

Also, in the shoulder ultrasound image, the controller 1300 may extract a third boundary of which an intensity changing degree of echo signals is less than the first threshold value but greater than a third threshold value, and determine the third boundary as an upper portion of the tendons. In addition, the controller 1300 may detect a thickness of the bursa based on a distance between the second and third boundaries.

When an interest region is selected, the controller 1300 may detect the fat layer based on echo signal intensity information of the interest region. Also, the controller 1300 may change a location or a size of the interest region based on a location of the fat layer or a location of the bursa.

The communication unit 1400 may include at least one component for allowing communication between the ultrasound diagnosis apparatus 10000 and a server 2000, the ultrasound diagnosis apparatus 10000 and a medical device 3000, and the ultrasound diagnosis apparatus 10000 and a mobile terminal 4000. For example, the communication unit 1400 may include a close-distance communication module 1410, a wired communication module 1420, and a mobile communication module 1430.

The close-distance communication module 1410 refers to a module for close-distance communication within a predetermined distance. Examples of close-distance communication technologies may include Wi-Fi, Bluetooth, Bluetooth low energy (BLE), ultra wideband (UWB), ZigBee, near field communication (NFC), Wi-Fi Direct (WFD), and infrared data association (IrDA).

The wired communication module 1420 refers to a module for communication using electric signals or optical signals. Examples of wired communication technologies according to an exemplary embodiment may include communication via a pair cable, a coaxial cable, an optical fiber cable, and an Ethernet cable.

The mobile communication module 1430 transmits or receives wireless signals to at least one selected from a base station, an external device (3000, 4000), or the server 2000 on a mobile communication network. The wireless signals may be voice call signals, video call signals, or various types of data for transmission and reception of text/multimedia messages.

The communication unit 1400 may be connected to a network 30 by wire or wirelessly to communicate with an external device (for example, first or second device 3000 or 4000) or the server 2000. The communication unit 1400 may exchange data with a hospital server or another medical apparatus in a hospital, which is connected thereto via a picture archiving and communication system (PACS). Furthermore, the communication unit 1400 may perform data communication according to the digital imaging and communications in medicine (DICOM) standard.

The communication unit 1400 may transmit or receive data related to diagnosis of the object 10, e.g., an ultrasound image, ultrasound image data, and Doppler data of the object 10, via the network 30 and may also transmit or receive medical images captured by another medical apparatus, e.g., a CT apparatus, an MRI apparatus, or an X-ray apparatus. Furthermore, the communication unit 1400 may receive information about a diagnosis history or medical treatment schedule of a patient from the server 2000 and utilize the received information for the diagnosis of the object 10.

The memory 1500 may store a program for processing the controller 1300 or data that is input or output (for example, ultrasound image data, information about a drug spreading boundary, information of a subject to be tested, probe information, or a body marker).

The memory 1500 may include at least one type of storage medium selected from a flash memory, a hard disk drive, a multimedia card micro type memory, a card type memory (for example, a secure digital (SD) or an XD memory), random access memory (RAM), static RAM (SRAM), read-only memory (ROM), electrically erasable programmable ROM (EEPROM), programmable ROM (PROM), a magnetic memory, a magnetic disc, and an optical disc. Also, the ultrasound diagnosis apparatus 10000 may manage a web storage or a cloud server that performs as a storage like the memory 1500 on the Internet.

The display unit 1600 displays information processed by the ultrasound diagnosis apparatus 10000. For example, the display unit 1600 may display an ultrasound image or a user interface (UI) or a graphical UI (GUI) related to a control panel.

According to an exemplary embodiment, the display unit 1600 may display location information of a bursa on a shoulder ultrasound image generated based on shoulder ultrasound image data. For example, the display unit 1600 may display a preset indicator at a location of the bursa on the shoulder ultrasound image. The display unit 1600 may display a first boundary line that distinguishes the bursa from a fat layer and a second boundary line that distinguishes the bursa from tendons.

When the display unit 1600 and a touch pad are layered and thus provided as a touch screen, the display unit 1600 may be used as not only an output device but also as an input device. The display unit 1600 may include at least one selected from a liquid crystal display (LCD), a thin film transistor LCD, an organic light-emitting diode (OLED) display, a flexible display, a 3D display, and an electrophoretic display. Also, according to the embodiments of the present inventive concept, the number of display units 1600 included in the ultrasound diagnosis apparatus 10000 may be two or more.

A method according to exemplary embodiments may be implemented through program instructions that are executable via various computer devices and recorded in computer-readable recording media. The computer-readable recording media may include program instructions, data files, data structures, or a combination thereof. The program instructions may be specifically designed for the present inventive concept or well-known to one of ordinary skill in the art of computer software. Examples of the computer-readable recording media include magnetic media (e.g., hard disks, floppy disks, or magnetic tapes), optical media (e.g., CD-ROMs or DVDs), magneto-optical media (e.g., floptical disks), and hardware devices specifically designed to store and execute the program instructions (e.g., ROM or RAM). Examples of the program instructions not only include machine codes that are made by compilers but also computer-executable high level language codes that may be executed by using an interpreter.

As described above, according to the one or more of the above exemplary embodiments, labels may be more accurately and conveniently edited with regard to geometric shapes of labels generated on a 3D ultrasound image.

The followings are another description of various embodiments according to the present invention. The present invention will be understood more in detail referring to the below description. Square brackets indicate references listed at the end of this specification.

SECTION 1. INTRODUCTION

A common problem encountered in computer vision is the model fitting with data that may be contaminated with noise and outliers. The "hypothesize-and-verify" framework is the core of many robust geometric fitting methods. The Random Sample Consensus (RANSAC) algorithm [3] is a widely used robust estimation technique, and most of the state-of-the-art methods are based on random sampling. They involve iterative loop of two steps: of random hypotheses generation and verification. A minimal subset of the input data points is randomly sampled and used to hypothesize model parameters. In the verification step, the hypotheses are evaluated against all the data and their support is determined.

There are two main drawbacks to random sampling-based techniques. The first problem is that it is difficult in general to determine the number of iterations to achieve a desired confidence without a priori knowledge such as inlier ratio and inlier scale. The true inlier ratio and true inlier scale is usually unknown in most realistic applications. When the number of iterations computed is limited, therefore, the estimated solution may not be reliable. The existence of multiple structures makes the problem more difficult since the inliers belonging to other structures are regarded as outliers (pseudo-outliers).

The second problem is the inconsistency of results, which is related to the first problem. If the number of iterations is insufficient, the random sampling-based techniques provide varying results for the same data and parameter settings. Despite the robustness of the algorithm, the random sampling-based methods provide no guarantee of consistency in their solutions due to the randomized nature of the algorithm [2].

Many advanced random-sampling methods have the same limitations of unreliability and inconsistency. There have been approaches to improving the efficiency of random hypothesis generation for the estimation of single structure [4, 6, 7, 8, 9, 10]. They have been developed to increase the frequency of hitting all-inlier samples.

To deal with multiple structure data, guided sampling techniques have been developed [11, 12, 13, 14, 15]. They generate a series of tentative hypotheses are generated from minimal subsets of the data in advance and carry out guided sampling based on preference analysis. The performance of these methods can be relatively low since the quality of the initial hypotheses may be bad when the outlier ratio is considerably high. Other multiple-structure model fitting methods also start with random hypothesis generation [16, 17, 18, 5, 19, 14, 20].

Due to the non-deterministic nature of random sampling, the quality of the hypotheses generated by all the methods mentioned above depends on the proportion of pseudo-outliers and gross outliers. Thus, reliable and consistent performance may not be expected when a priori knowledge is unknown. The recent methods such as [21, 22, 23, 24] removes the dependency on inlier scale for random sampling-based approach. Nevertheless, they cannot overcome the inherent limitation of random sampling.

Deterministic optimization has recently been actively investigated for model fitting problems in computer vision [2, 25, 26, 27, 28]. Despite the guarantee for globally optimal solution, the main limitation of the global optimization algorithms lies in their computational inefficiency. The presence of image features from multiple structures makes their computation cost even higher. Besides, there has been no deterministic method considering inlier scale estimation for model fitting problems.

In this paper, we present a deterministic hypothesis generation algorithm for robust fitting of multiple structures. The goal of our method is to generate reliable and consistent hypotheses with reasonable efficiency based on the maximum feasible subsystem (MaxFS) framework. There are two limitations in using a MaxFS algorithm for hypothesis generation. First, its performance depends on the user-specified inlier scale. We present an algorithm, called iterative MaxFS with inlier scale (IMaxFS-ISE), that iteratively estimates model parameters and inlier scale. The second limitation is the computational inefficiency mentioned above. We circumvent this limitation by establishing MaxFS problems only with subsets of data but not the whole data. The IMaxFS-ISE algorithm initially solves the MaxFS problem for generating model hypothesis only with a top-n ranked subset based on matching scores. In the refinement stages, on the other hand, it utilizes the matching scores and residuals from the previous hypothesis for selecting subsets. This reduction of data for the MaxFS problem makes our algorithm computationally realistic.

The strength of our method is that it can stably select inliers of a major structure against outliers given a subset of data as long as a good inlier scale is given since it is based on a global optimization method. It provides a reliable and consistent hypothesis for each genuine structure regardless of inlier ratio and the number of structures unlike the existing methods that use random sampling. Therefore, there is no need for additional processing such as hypothesis filtering or merging since our method generates a reliable hypothesis for each structure.

Figure 8:
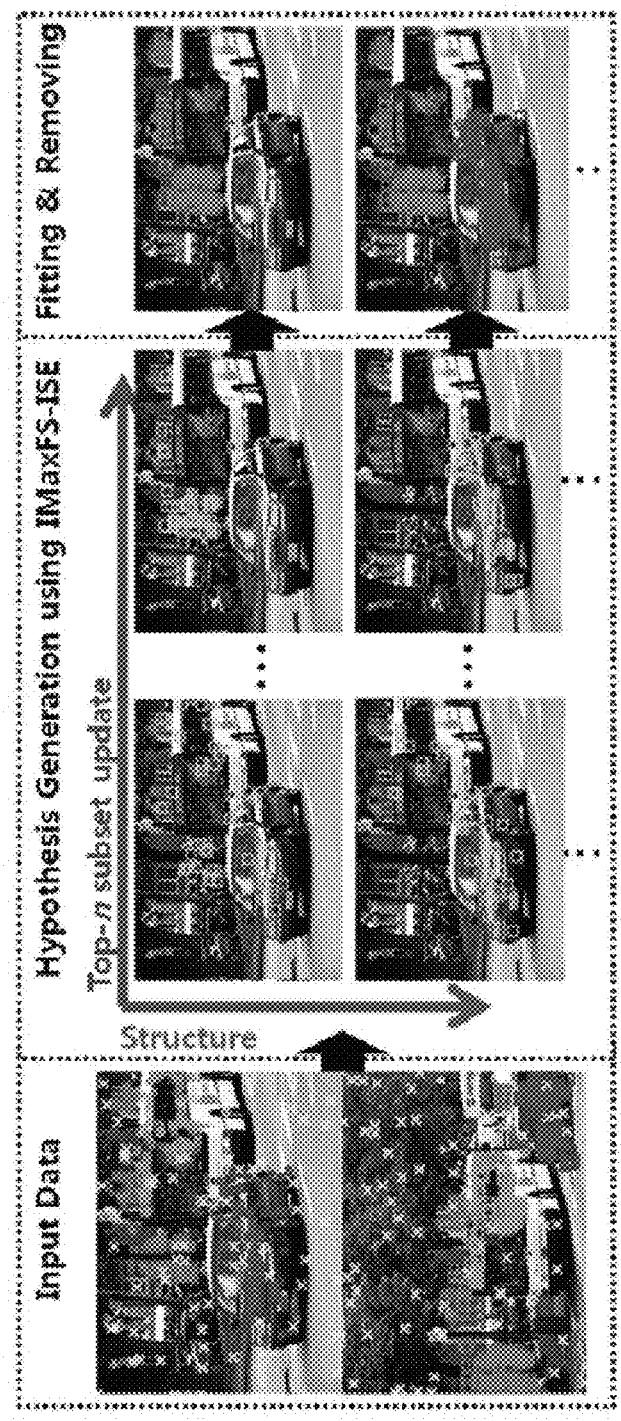
FIGS. 8 through 20 are diagrams regarding model fitting according to various exemplary embodiments.

The presented algorithm adopts a sequential "fitting-and-removing" procedure. In our method, only one hypothesis is generated for each genuine structure. When a new hypothesis is added, hypothesis selection for each data are performed via the optimization of an energy function and the inliers for each hypothesis generated up to present are removed from whole data. This procedure is repeated until overall energy function is not decreased any more. FIG. 8 provides an overview of our algorithm. In the input data, yellow crosses indicate the gross outliers, and other color markers indicate different structures. In the middle of the FIG. 8, each row shows that top-n ranked subset for each structure is updated. Cyan squares indicate the top-n ranked subset. In the right of the FIG. 8, results of fitting are shown.

There have been approaches to using the feature matching scores to increase the chance of finding all-inlier sample [8, 9]. However, they cannot guarantee that correspondences with high matching score are drawn from the same structure. There also has been an approach to the use of fitting residuals for ranking data in selecting a subset for hypothesis generation [12].

Our method has specific advantages. Our method always guarantees that the model hypothesis from the current subset is the best model while the guided sampling of the [12] cannot be convinced that current hypothesis is generated from an uncontaminated minimal subset.

The rest of paper is organized as follows: Section 2 introduces an IMaxFS-ISE method. Section 3 describes our algorithm based on fitting-and-removing procedure. Section 4 shows the experimental results on real data, and we conclude in Section 5.

SECTION 2. ITERATIVE MAXIMUM FEASIBLE SUBSYSTEM WITH INLIER SCALE ESTIMATION

In this section, we describe main optimization techniques that we employ in our method.

Section 2.1 MaxFS Formulation for Geometric Fitting

The aim of a MaxFS framework is to find the largest cardinality set with constraints that are feasible [2, 26]. The objectives of the MaxFS and RANSAC are the same. However, the MaxFS guarantees a global solution unlike the ---
Algorithm 1. Iterative MaxFS with inlier scale estimation
$[\theta^*, s^*, l^{in*}] = $ IMaxFS-ISE(X, M, K)

Input: input data X, M(for MaxFS), initial inlier scale $s_0$ and K value (for IKOSE)
Output: hypothesis parameter $\theta^*$, inlier scale $s^*$ and the number of maximum inliers $l^{in*}$
1:   Initialize the inlier scale: $s_0$ (small value)
2:   While(until $s_t$ converges)
3:       Estimate parameter $\theta_t$ and the number of inliers $l^{in}_t$ in X using MaxFS with $s_t$. (Sec. 2.1).
4:       If $l^{in}_t > l_{th}^{in}$ (We set $l_{th}^{in} = 10$)
5:           Estimate inlier scale $s_{t+1}$ using IKOSE(X, K) using Equation 3 (Sec.2.2).
6:       Else
7:           $s_{t+1} = s_t + \epsilon$
8:       End if
9:       $\theta^* = \theta_t$, $l^{in*} = l^{in}_t$ and $s^* = s_t$
10:  End while

---

RANSAC. The MaxFS problem admits the mixed integer linear programming (MILP) formulation. The MILP problem is known to be NP-hard. Hence, only relatively small problems can be solved practically. While the exact MILP formulation is useful for small models, it is not effective on large models due to its computational inefficiency [1].

We use the algebraic Direct Linear Transformation (DLT) to estimate hypothesis parameters [29]. We then can formulate the DLT-based geometric fitting problem as a MaxFS problem. The set of input data X is partitioned into the inlier-set $X^I$ and the outlier-set $X^O$ with $X^I \subseteq X$, $X^O \subseteq X$, $X^I \cup X^O = X$ and $X^I \cap X^O = \emptyset$.

A maximum inlier scale s provides a bound for the algebraic residual $d_i = |a_i^T \Theta|$ at point i, where $a_i^T$ is each row vector of A in the homogeneous equation $A\Theta = 0$:

$$d_i = |a_i^T \Theta| \leq s, \; s > 0. \tag{1}$$

MaxFS formulation of Equation 1 is as follows:

$$\{\hat{\Theta}^{MaxFS}, \hat{y}\} = \underset{\Theta, y}{\mathrm{argmin}} \sum_{i=1}^{k} y_i \tag{2}$$

subject to $|a_i^T \Theta| \leq s + M_i y_i, \; \forall \; i$ $c^T \Theta = 1,$ $\Theta \in \mathfrak{R}^n, \; y_i \in \{0, 1\}, \; i = l, \ldots, k.$ where $M_i$ is a large positive number (Big-M value).

The case where $y_i = 0$ indicates that the $i^{th}$ data is an inlier. If $y_i = 1$, the $i^{th}$ data is an outlier and the corresponding constraint is deactivated automatically. We use a linear constraint $c^T \Theta = 1$, rather than the commonly used $\|\Theta\| = 1$, where c is a problem dependent vector determined by the user [29]. Our MaxFS algorithm solves Equation 2 for input data X. Then, hypothesis $\hat{\Theta}^{MaxFS}$ is generated from the maximum inlier-set.

Section 2.2. Iterative MaxFS with Inner Scale Estimation (IMaxFS-ISE)

The MaxFS problem for geometric fitting can be exactly solved when true inlier scale is known. However, true inlier scale s is unknown in many practical situations, which is commonly set manually by users. In our algorithm, on the other hand, we include a method for estimating the inlier scale from data in a similar iterative manner that has been shown in [24]. Recent work [24] has proposed a robust scale estimator called IKOSE which can accurately estimate the scale of inliers for heavily corrupted multiple-structure data.

Given the true parameters of the Jth structure ($\theta^J$), the inlier scale $\hat{s}_K^J$ and the inlier number of Jth structure $v^J$ can be estimated by IKOSE. IKOSE for the Jth structure can be written as follows:

$$\hat{s}_K^J = \frac{|\tilde{r}_K^J|}{\Phi^{-1}\left(\frac{1}{2}(1 + \kappa^J)\right)}, \tag{3}$$

$$\kappa^J := K / v^J, \tag{4}$$

where $|\tilde{r}_K^J|$ is the kth sorted absolute residual given the parameters of the Jth structure ($\theta^J$) and $\Phi^{-1}(\bullet)$ is the argument of the normal cumulative density function and $v^J$ is the number of points satisfying $|r_i^J / \hat{s}_K^J| < 2.5$.

When true inlier scale is known, correct model parameters can be estimated by solving the MaxFS problem. In other words, when true model parameters are known, accurate inlier scale can be estimated from IKOSE. To solve this problem, we propose an iterative scheme. Our IMaxFS-ISE method is summarized in Algorithm 1.

We set the initial inlier scale $s_0$ to a small value to guarantee that initial model parameter estimate is not badly biased. In the iteration procedure, the estimated inlier scale $s_t$ increases with the iteration step t until it reaches the true inlier scale and the estimated model parameters reach the true model parameters.

SECTION 3. FITTING AND REMOVING PROCEDURE FOR MULTI-STRUCTURE FITTING

In this section, we describe our deterministic algorithm for robust fitting of multiple structures. It is summarized in Algorithm 2.

Section 3. 1 Fitting-and-Removing Procedure

Our goal is to estimate the parameters $\Theta = \{\theta_l\}_{l=1}^{L}$ and the

---

Algorithm 2. Fitting-and-Removing Procedure

Input: input data $X_N$, M(for MaxFS), initial Kvalue (for IKOSE) $K^{(0)}$ and the number of data points in subset n
Output: hypotheses parameter set $\Theta = \{\theta^*_l\}_{l=1}^{L}$ and $S = \{\sigma_l^*\}_{l=1}^{L}$
1:  $\Theta = \emptyset$, $S = \emptyset$, $X_{RD} = X_N$ and $l = 1$
2:  While ( until $E(f_{l-1}) < E(f_l)$ )
3:    $h = 1$ and $K_l^{(h-1)} = K^{(0)}$
4:    Initialize top-n ranked subset $X_n^{(h-1)}$ from $X_{RD}$
5:    While (until the number of inliers is not changed)
6:      Estimate hypothesis parameter using
        $[\theta_l^{h*}, s_l^{h*}, l^{ln}l^{h*}]$=IMaXFS-ISE$(X_n^{(h)}, M, K_l^{(h)})$ (Sec. 2.2).
7:      Estimate inlier scale $\sigma_l^{h*}$ using IKOSE$(X_N, K_l^{(h)})$
8:      Calculate inlier probability $P(x_i)$ (Sec.3.2)
9:      Update top-n ranked subset $X_n^{(h+1)}$ from $X_{RD}$
10:     $K_l^{(h+1)} = l^{ln}l^{h*}$
11:     $h = h + 1$
12:   End while
13:   $\Theta = \Theta \cup \{\theta_l^{h*}\}$ and $S = S \cup \{\sigma_l^{h*}\}$
14:   Obtain labels $f_l$ via $\alpha$-expansion (Sec. 3.1)
15:   Generate the reduced data $X_{RD}$ (Sec. 3.2)
16:   $l = l+1$
17: End while

--- inlier scale $S = \{\sigma_l\}_{l=1}^{L}$ for multiple structures from input data $X_N = \{x_i\}_{i=1}^{N}$. The parameters and inlier scale of the hypothesis for each structure is deterministically estimated using the IMaxFS-ISE. Moreover, only one reliable hypothesis is generated for each structure unlike random sampling-based methods which generates a large number of hypotheses. This facilitates the use of the "fitting-and-removing" procedure.

Our algorithm consists of three major steps: hypothesis generation, labeling and removing inliers. We repeat over these steps until the overall energy function does not decrease. At each iteration stage, a new hypothesis corresponding to a new structure is generated and added to $\Theta$. After a new hypothesis is added, a set of labels $f = \{f_i\}_{i=1}^{N}$ assign each data $x_i$ either to one of the structures or to an outlier by minimizing an objective function using the a-expansion optimization [20]. Our objective function is defined as follows:

$$E(f) = \sum_{i=1}^{N} D(x_i, f_i) + \sum_{\langle i,j \rangle \in N} V(f_i, f_j) + O(f). \tag{5}$$

The data cost $D(x_i, f_i)$ in Equation 5 is formulated as $$D(x_i, f_i) = \begin{cases} r(x_i, \theta_{f_i}) & \text{if } f_i \in \{1, \ldots, L\}, \\ \sigma_{l^*} & \text{if } f_i = 0, \end{cases} \tag{6}$$

$$l^* = \underset{l}{\mathrm{argmin}} \, r(x_i, \theta_l), \tag{7}$$

where $r(x_i, \theta_{j*})$ is the absolute residual of $x_i$ after fitting the structure $\theta_{j*}$ and $\sigma_{j*}$ is the inlier scale estimated from the structure $\theta_{j*}$ which is the penalty for labeling $x_i$ as an outlier. The smoothness cost $v(f_i, f_j)$ in Equation 5 penalizes $f_i \neq f_j$ in some manner. We construct a neighborhood graph from the Delaunay Triangulation on input data $X_N$ as [15, 20]. The label cost $O(f)$ is proportional to the number of structures l in $\Theta$ and penalize overly complex models. After labeling is performed for the set of hypotheses $\Theta$ at an iteration stage, a reduced input data $X_{RD}$ is generated by removing all the estimated inliers from input data $X_N$. At the next iteration stage, the hypothesis is generated from the reduced input data $X_{RD}$.

Section 3.2. Hypothesis Generation Using IMaxFS-ISE from Subset with Top-n Ranked Data We now describe our hypothesis generation method based on the IMaxFS-ISE algorithm. It splits a large problem into smaller ones making the IMaxFS-ISE algorithm efficient. Hypothesis generation consists of three steps. The first step is to calculate inlier probability $P(x_i)$ for $x_i$. In the second step, the inlier probability is used to sort the input data $X_{RD}$ and update the top-n ranked subset $X_n^{(h+1)}$. The last step is to estimate the parameters of the hypothesis $\theta_l^{h*}$ performing the IMaxFS-ISE algorithm on the top-n ranked subset. These steps are repeated until the number of inliers is not changed.

The initial subset $X_n^{(0)}$ consists of n data with the highest matching scores among the input data $X_{RD}$. It will contain mostly inliers from the several structures but it is unknown where each inlier belongs. Given $X_n^{(0)}$, the maximum inliers are estimated with the IMaxFS-ISE algorithm and they are used to generate initial hypothesis. For a subset, a MaxFS method guarantees that the maximum inliers are found as long as the number of inliers is larger than the minimum number required for estimating model parameters. When the inliers from a structure are not enough or spatially restricted on a small region, the initial hypothesis can significantly deviate from the true structure. To refine the hypothesis in the next stage, new inlier probabilities for the input data $X_{RD}$ is computed and the top-n ranked subset $X_n^{(h+1)}$ is updated based on them.

Given a hypothesis $\theta_l^h$, we compute the inlier probability of $x_i \in X_{RD}$ as follows:

$$P(x_i) \propto P(x_i|q)P(x_i|\theta_l^h) = q(x_i)\frac{1}{Z}\exp\left(\frac{-r(x_i, \theta_l^h)^2}{2\sigma_l^{h2}}\right), \quad (8)$$

where $q(x_i)$ is the normalized matching score for the input $x_i$, $r(x_i, \theta_l^h)$ is the absolute residual of $x_i$ computed with the hypothesis $\theta_l^h$ generated for the lth structure in the hth iteration, $\sigma_l^h$ is the inlier scale corresponding to the hypothesis $\theta_l^h$, and Z is a normalization constant. After the IMaxFS-ISE step is finished in the hth iteration, $\sigma_l^h$ is estimated from whole dataset $X_N$ using IKOSE. Note that $\sigma_l^h$ is different from the inlier scale $s_l^h$ which is estimated from the subset $X_n^{(h)}$.

Figure 9A:
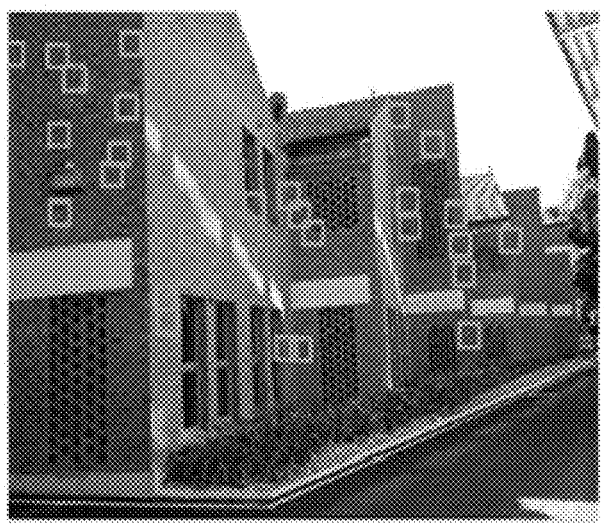
Figure 9B:
Figure 9C:
Figure 10A:
Figure 10B:
Figure 11:
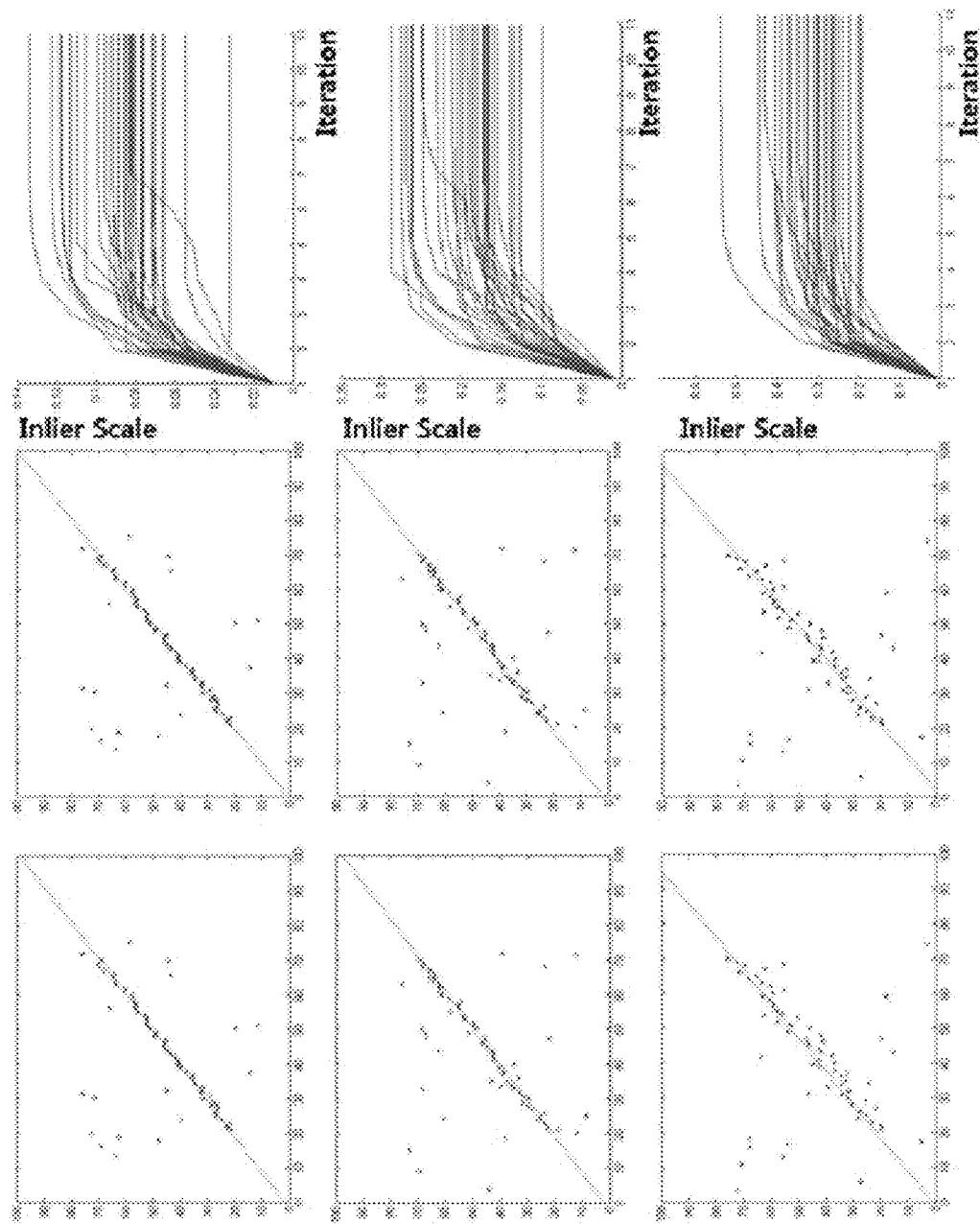
Figure 12A:
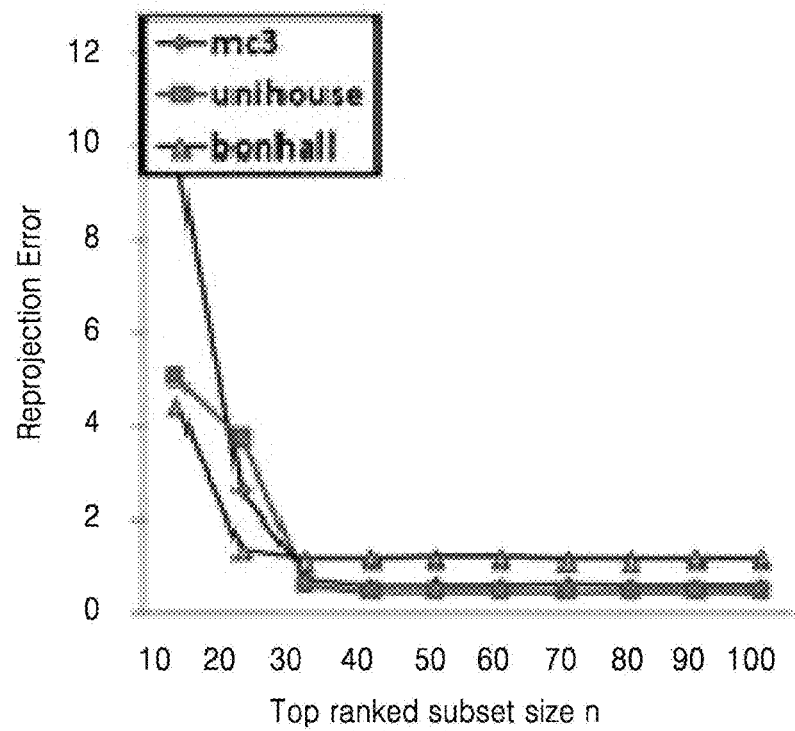
Figure 12B:
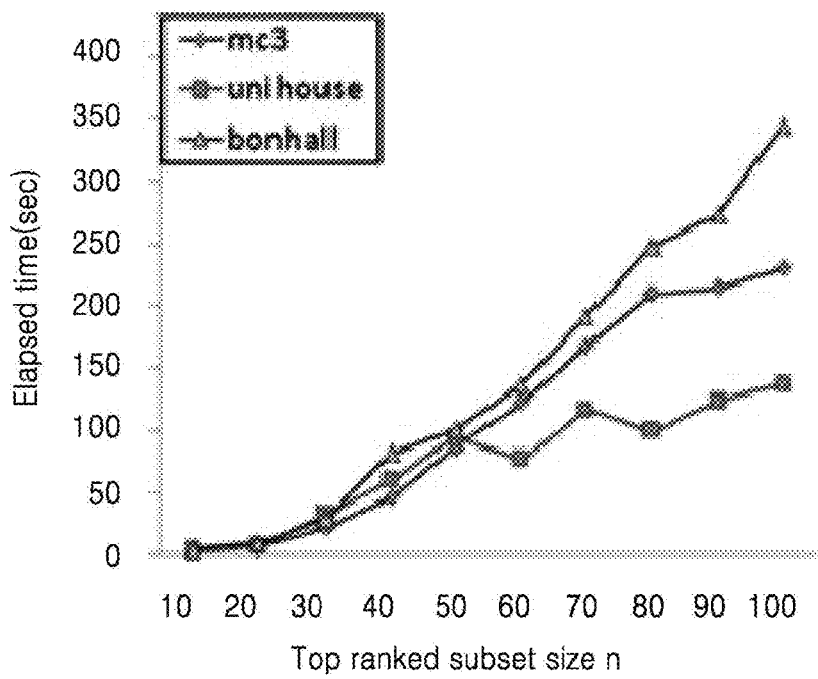
Figure 12C:
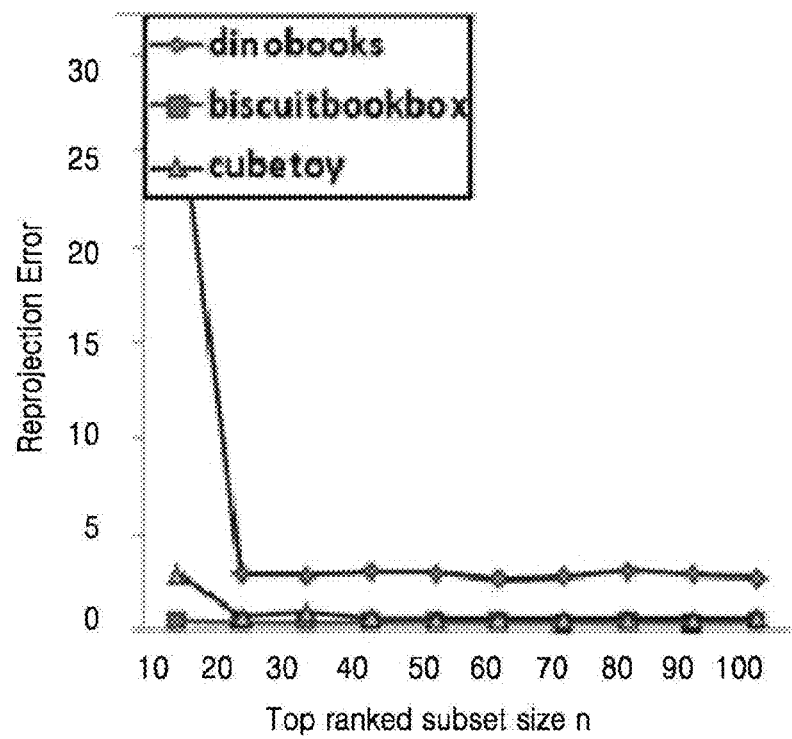
Figure 12D:
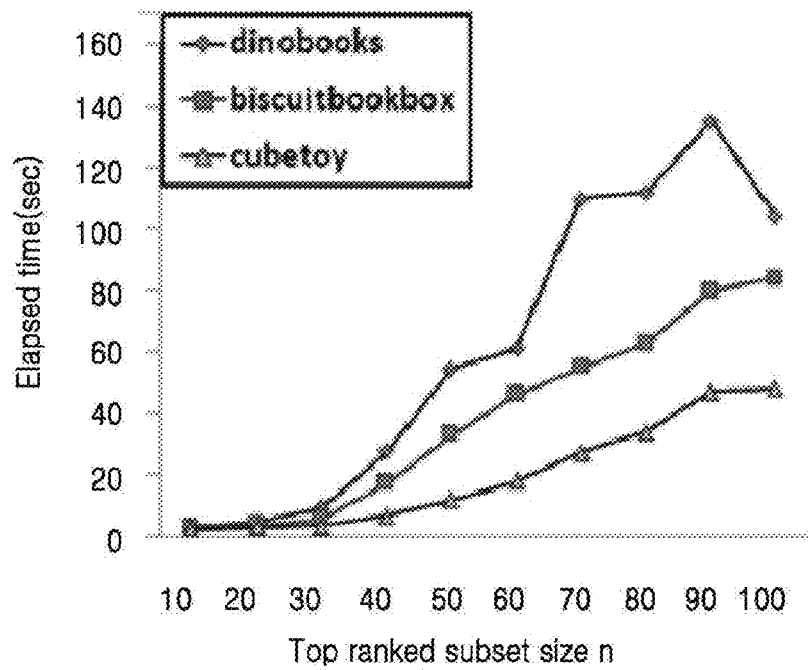

The use of both the inlier scale $\sigma_l^h$ and the matching score $q(x_i)$ in Equation 8 results in more reliable subset than that of only residuals for data ranking. If a subset mainly consists of data with small residuals, its inliers are often distributed only in small regions. On the other hand, the inliers in the subset selected with the matching score as well as the residual tend to be more spread out spatially over the structure. FIG. 10 shows an example where inliers are widely distributed in space when the matching scores are used. If $\theta_l^h$ is a good hypothesis, $\theta_l^{h+1}$ is made better since the $X_n^{(h+1)}$ includes more inliers. Although $\theta_l^h$ is badly biased, the inliers of other structures can be included in the top-n ranked subset instead of the outliers with small residuals if matching scores are used for data ranking. FIG. 9 shows the initial top-n ranked subset, an updated subset after several iterations and the final subset.

One important issue in IMaxFS-ISE is how to choose K. To include as many inliers as possible, K should be set to the largest possible value that does not yield breakdown. In our algorithm, $K_l^{(h+1)}$ is set to $1^{ln}{}_l^{h*}$ which is the number of maximum inliers estimated from the previous IMaxFS-ISE procedure. On the other hand, we conservatively set the initial value $K^{(0)}$ to a small value, e.g., 10.

SECTION 4. EXPERIMENTAL RESULTS

We have implemented our algorithm in MATLAB using the LP/MILP solver GUROBI [30] which provides functions for the LP/MILP and a desktop with Intel i5-2500 3.30 GHz (4 cores) and 3 GB RAM is used for experiments. We tested five methods including ours on several real datasets. For performance evaluation and comparison, we measured the actual elapsed computation time. Images and keypoint correspondences were acquired from the Oxford VGG dataset [31] and the Adelaide RMF dataset [34, 35]. We used manually labeled keypoint correspondences which were obtained by SIFT matching. If keypoint matching scores are not available, we assigned a proper matching score to each correspondence.

Section 4.1. IMaxFS-ISE: Line Fitting Results

We performed the DLT-based IMaxFS-ISE algorithm to fit a 2D line for data with different inlier scales. We set the initial inlier scale $s_0$ to 0.01. A line includes 60 inliers with Gaussian noise and gross outliers, and the number of gross outliers is fixed at 40. Noise level is varies from 0.1 to 0.3.

FIG. 11(A) through (I) shows the example of the results with initial inlier scale (first column), the example of the results with final inlier scale (second column) and the transitions of inlier scales during iteration (third column). For each noise level (0.1, 0.2 and 0.3), the experiments were performed for 30 datasets with different Gaussian noise and random outliers. Red points indicate estimated outliers and blue points indicate estimated inliers. The results show the estimated inlier scale is well-converged on a reliable inlier scale value in most cases.

Section 4.2. IMaxFS-ISE: Homography and Affine Fundamental Matrix Estimation

We performed the DLT-based IMaxFS-ISE to estimate planar homography and affine fundamental matrix for each data subset. For our IMaxFS-ISE algorithm, the Big-M value in Equation 2 was set to 10000, the initial $K^{(0)}$ value and $I_{th}^{ln}$ were set to the fixed value of 10.

To determine the parameters n (subset size) and $s_0$, we experimentally examined the effects of parameter n (subset size) on re-projection error. We investigated the effect of n in the range of [10 100] on data with different outlier rates. FIGS. 12 (a) and (b) show the re-projection errors and the computation time for homography estimation with the IMaxFS-ISE method as the subset size n is increased. Only the results from three datasets are shown in the plots. FIGS. 12 (c) and (d) show the re-projection errors and the computation time for affine fundamental matrix estimation as the subset size n is increased. It can be seen in FIGS. 12(a) though (d) that high accuracy is achieved for the subset size n from about 30 up and the computation time gradually increases with n. For the IMaxFS-ISE algorithm, therefore, we set n to 30 to attain both accuracy and computational efficiency.

Figure 13A:
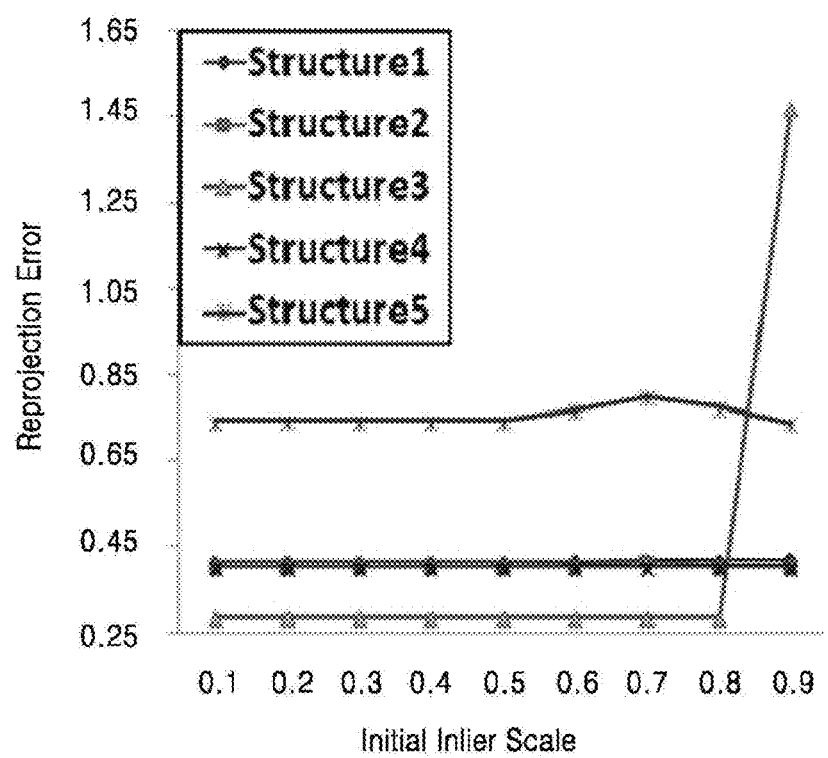
Figure 13B:
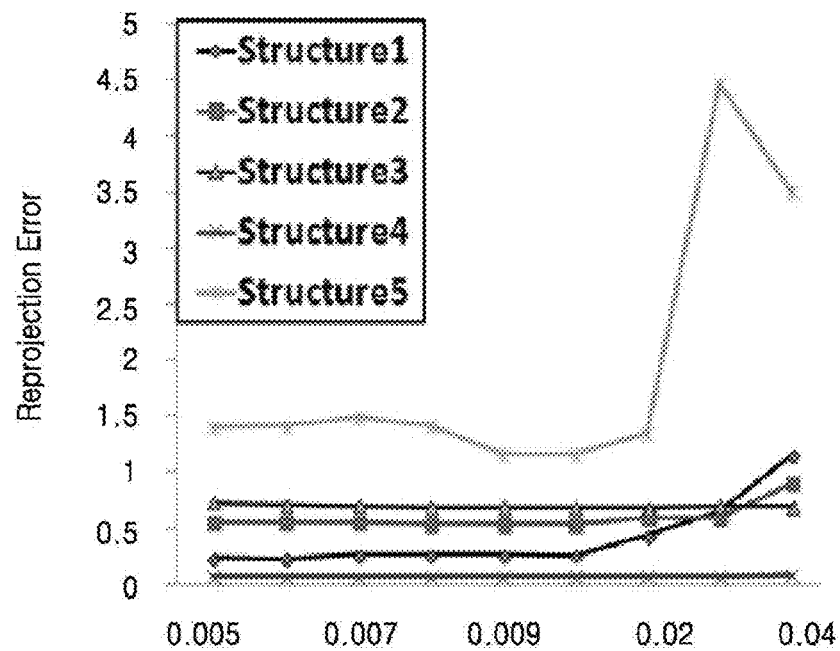

We investigated the effect of initial inlier scale $s_0$ on re-projection error for five different structures in three datasets. FIGS. 13 (a) and (b) show the results for homography and affine fundamental matrix which demonstrate that our algorithm is stable for a wide range of the initial inlier scale $s_0$. If $s_0$ is too small, the computation time becomes too long since our method performs the MaxFS algorithm increasing the inlier scale gradually until $I^{in}_i > I^{in}_{th}$. We find that the $s_0$ values of 0.5 and 0.01 for the estimation of homography and fundamental matrix, respectively, are the good compromises between stability and computational efficiency for all the datasets we tested.

Figure 14A:
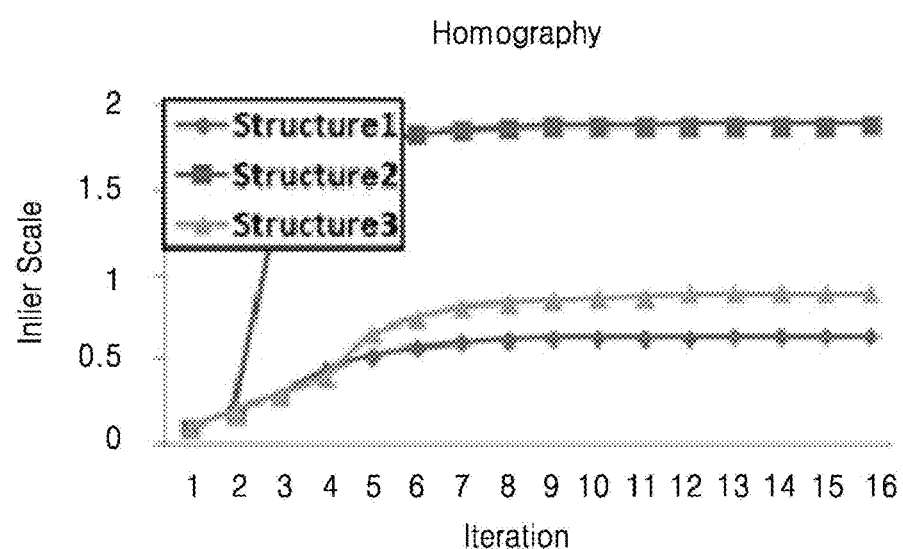
Figure 14B:
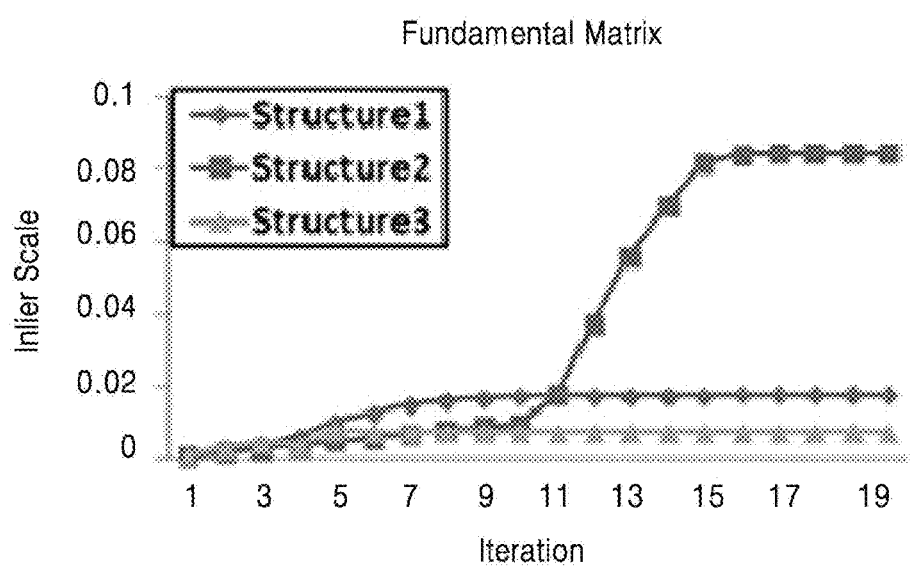
Figure 15:
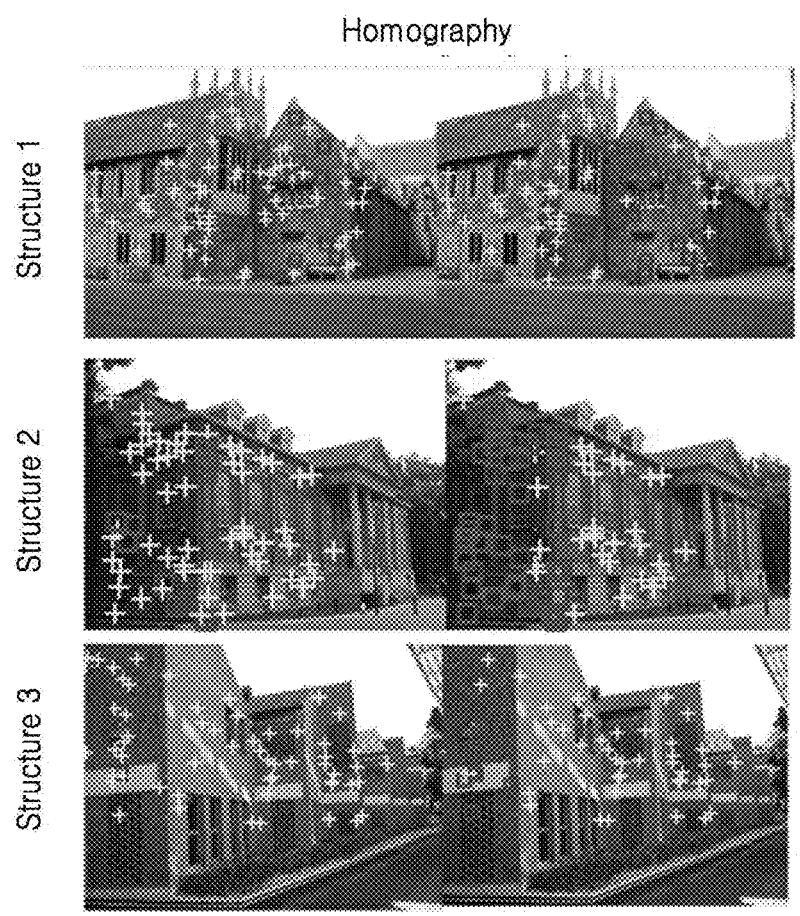
Figure 16:
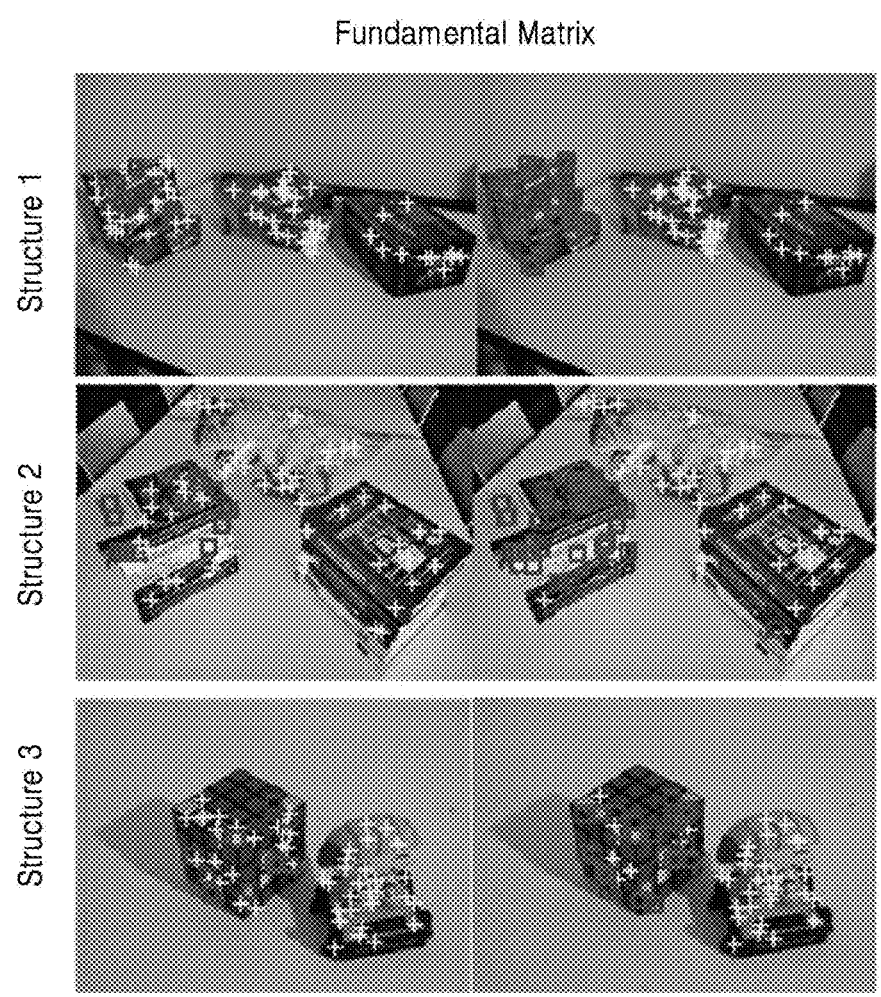

FIG. 15 and FIG. 16 show the inlier estimation with IMaxFS-ISE at the initial and final iteration stages. In each figure, the left images show the inliers estimated from IMaxFS-ISE at the first iteration and the right images show the final results. In these experiments, we performed the IMaxFS-ISE algorithm on one subset with 70 data points in each dataset. The transition of the inlier scale during iteration for each structure in FIG. 15 and FIG. 16, is shown in FIG. 14.

Note that we should set initial inlier scale $s_0$ to be a small value to avoid breakdown caused by gross outliers or inliers in other structure. If initial inlier scale $s_0$ is too large, the IMaxFS-ISE algorithm cannot obtain good result since initial hypothesis can be badly biased.

Figure 17:
Figure 18:
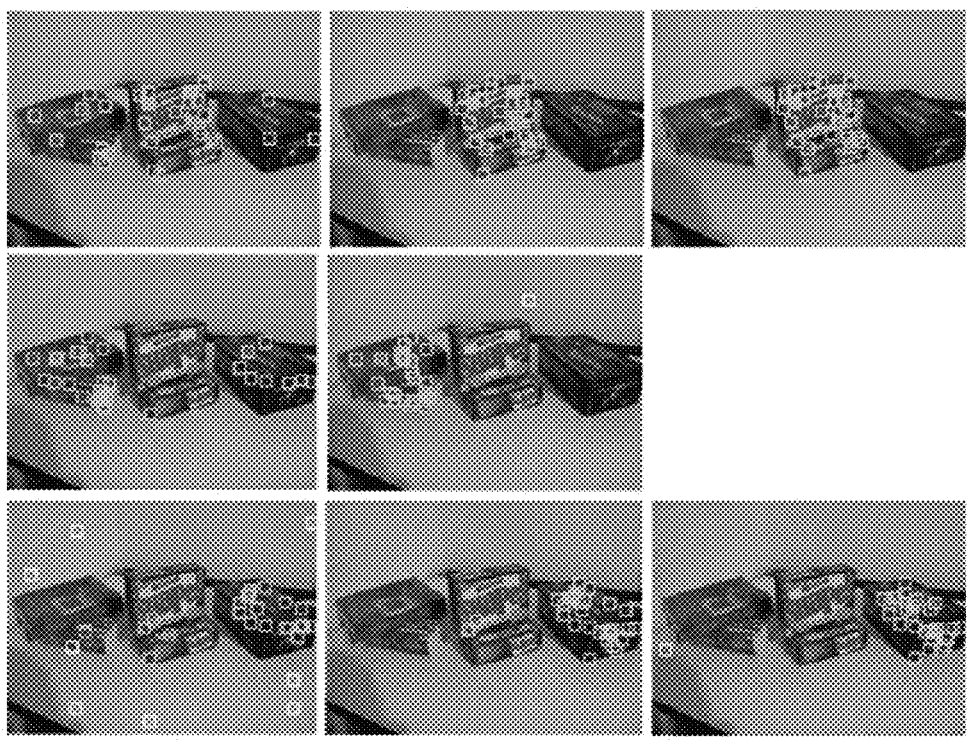
Figure 19:
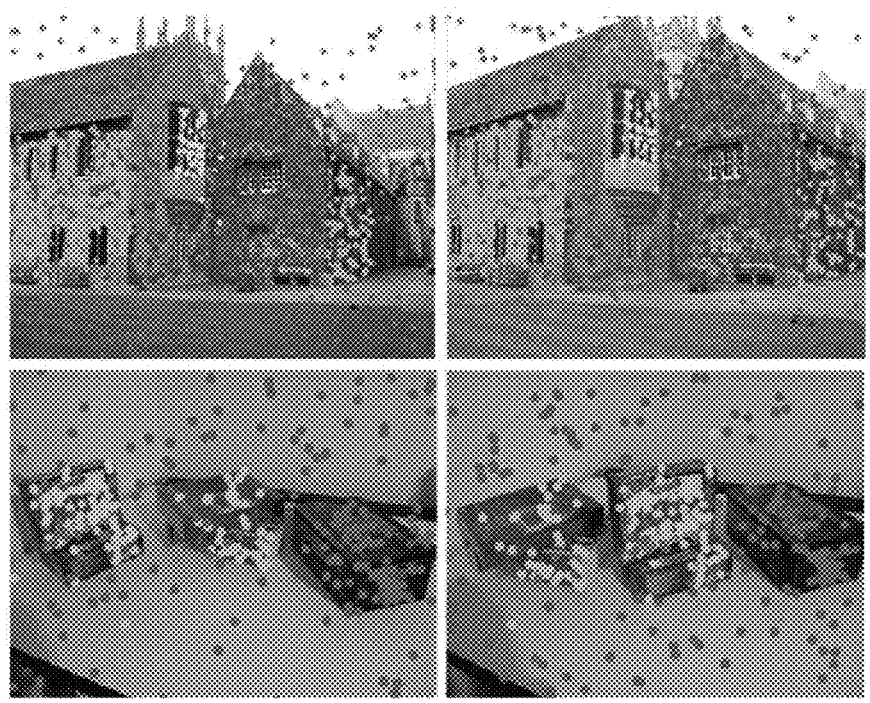

FIG. 19 shows final fitting results for datasets shown in FIG. 17 and FIG. 18.

Section 4.4. Comparison with Random Sampling Approaches

Our algorithm is compared with four other methods based on random sampling: uniform random sampling (RANSAC) [32, 3], PROSAC [9], Multi-GS [11, 33] and the state-of-the-art algorithm RCM [15, 37]. We implemented the PROSAC algorithm in MATLAB.

For performance evaluation, we measured elapsed computation time and the number of generated hypotheses (L) and computed the re-projection errors (mean and standard deviation). The results for the five algorithms are summarized in Tables 1 and 2 with the best results boldfaced.

For each label/structure, the hypothesis that shows the minimum re-projection error is selected. Overall error was calculated by averaging re-projection errors for all the structures. For RANSAC, PROSAC and Multi-GS, 50 random sampling runs were carried out. The three algorithms were performed for similar amounts of computational time (elapsed computation time) with computational time for our method. Since our method and RCM runs till completion of algorithm, the elapsed computation time for our method and RCM were not limited but measured. For RCM, the average of computation times are measured.

Homography Estimation

Table 1 summarizes the performance of five methods for estimating planar homography for five datasets.

TABLE 1

Performance of various methods on homography estimation for the several real datasets.

| Data | OR [%] | Method | RANSAC | PROSAC | Multi-GS | RCM | IMaxFS-ISE |
|---|---|---|---|---|---|---|---|
| raglan | 10 | Elapsed time [sec] | 70 | 70 | 70 | 8.352 | 69.5471 |
|  |  | Mean | 0.8565 | 1.3974 | 1.0313 | 0.8456 | 0.8178 |
|  |  | Std | 0.0761 | 0.0649 | 0.0942 | 0.7225 | 0 |
|  |  | L | 30014 | 30577 | 1410 | 9 | 11 |
| mc3 | 10 | Elapsed time [sec] | 25 | 25 | 25 | 4.6127 | 24.3706 |
|  |  | Mean | 1.1645 | 1.241 | 1.5296 | 2.0281 | 0.4598 |
|  |  | Std | 0.0927 | 0.079 | 0.232 | 0.2099 | 0 |
|  |  | L | 15052 | 12815 | 985 | 5 | 7 |
| library | 70 | Elapsed time [sec] | 20 | 20 | 20 | 1.6123 | 19.15 |
|  |  | Mean | 1.1518 | 0.9468 | 0.9739 | 2.8468 | 0.8658 |
|  |  | Std | 0.2193 | 0.0145 | 0.1706 | 3.4552 | 0 |
|  |  | L | 17749 | 17604 | 2031 | 5 | 3 |
| unihouse | 30 | Elapsed time [sec] | 20 | 20 | 20 | 7.4608 | 20.42 |
|  |  | Mean | 1.5419 | 1.3743 | 1.8665 | 4.4215 | 0.4621 |
|  |  | Std | 0.2855 | 0.0828 | 0.2641 | 2.6775 | 0 |
|  |  | L | 8748 | 10520 | 789 | 4 | 6 |
| bonhall | 30 | Elapsed time [sec] | 35 | 35 | 35 | 6.1367 | 36.22 |
|  |  | Mean | 1.0982 | 0.7331 | 1.5117 | 1.8345 | 1.274 |
|  |  | Std | 0.2076 | 0.0273 | 0.3292 | 2.7598 | 0 |
|  |  | L | 21056 | 20390 | 1327 | 6 | 6 |

Section 4.3. Results for Updating Top-n Ranked Subset

FIG. 17 and FIG. 18 show the updated subset for each structure in each iteration stage. As the quality of the estimated hypothesis is refined in each iteration stage, the inliers for each structure are increased progressively in the subset.

Cyan squares indicate inliers in the subset and yellow squares denote gross outliers in the subset.

The results demonstrate that our method yields reliable and consistent results with reasonable computational efficiency. Since our algorithm generates slightly more hypotheses than the number of structures, there is no need to reduce or merge the hypotheses generated.

Fundamental Matrix Estimation

Table 2 shows the performance of the algorithms for estimating affine fundamental matrix for five datasets.

TABLE 2

Performance of various methods on affine fundamental matrix estimation for the several real datasets.

| Data | OR [%] | Method | RANSAC | PROSAC | Multi-GS | RCM | IMaxFS-ISE |
|---|---|---|---|---|---|---|---|
| cubetoy | 20 | Elapsed time [sec] | 10 | 10 | 10 | 1.0403 | 7.244 |
|  |  | Mean | 0.6211 | 0.7185 | 0.6159 | 0.8578 | 0.6127 |
|  |  | Std | 0.0043 | 0.0493 | 0.0044 | 0.1155 | 0 |
|  |  | L | 13263 | 13586 | 2067 | 3 | 2 |
| carsbus | 40 | Elapsed time [sec] | 10 | 10 | 10 | 3.8849 | 9.5698 |
|  |  | Mean | 0.6772 | 0.7058 | 0.6806 | 1.4978 | 0.7678 |
|  |  | Std | 0.0016 | 0.0037 | 0.0191 | 0.453 | 0 |
|  |  | L | 6410 | 6238 | 1171 | 3 | 3 |
| dinobooks | 70 | Elapsed time [sec] | 20 | 20 | 20 | 11.6536 | 17.187 |
|  |  | Mean | 3.044 | 3.5394 | 2.7171 | 5.3322 | 2.7146 |
|  |  | Std | 0.3924 | 0.3497 | 0.4198 | 1.4298 | 0 |
|  |  | L | 9899 | 9163 | 1453 | 2 | 3 |
| 4B | 70 | Elapsed time [sec] | 15 | 15 | 15 | 64.5312 | 16.941 |
|  |  | Mean | 1.3576 | 1.2837 | 1.102 | 3.5178 | 1.0818 |
|  |  | Std | 0.1606 | 0.0678 | 0.1605 | 2.1612 | 0 |
|  |  | L | 2504 | 2500 | 668 | 1 | 6 |
| 5B | 10 | Elapsed time [sec] | 10 | 10 | 10 | 4.4897 | 12.152 |
|  |  | Mean | 0.2872 | 0.9137 | 0.2605 | 1.4975 | 0.3195 |
|  |  | Std | 0.0112 | 0.1273 | 0.0059 | 0.6388 | 0 |
|  |  | L | 1639 | 1442 | 492 | 3 | 6 |

The results clearly show that our algorithm deterministically generates high-quality hypotheses with reasonable efficiency. Note that the random sampling-based methods produce large variation in their results.

Figure 20:
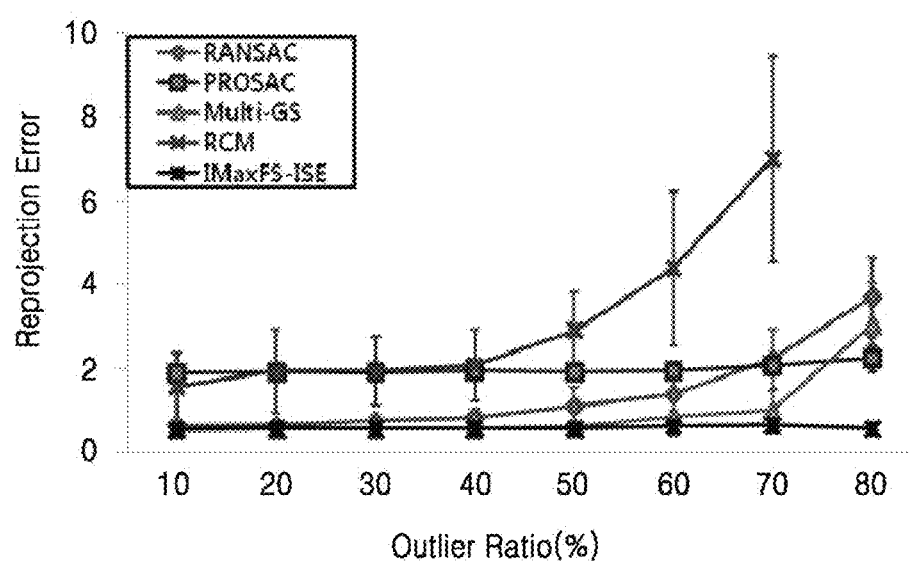

FIG. 20 shows the re-projection errors produced by the five methods on BCD data as outlier ratio is increased. Our algorithm outperforms the other algorithms as outlier ratio is greatly increased. Since the probability of hitting an all-inlier subset is decreased with the random sampling-based approaches as the outlier ratio is increased, the errors are increased substantially. On the other hand, the hypothesis generated by the IMaxFS-ISE algorithm is little influenced by the outlier ratio.

SECTION 5. CONCLUSION

We present a novel deterministic approach to reliable and consistent hypothesis generation for multiple-structure model fitting. Instead of generating hypothesis based on random sampling, we make a deterministic optimization method computationally realistic by utilizing only top-n ranked subsets and providing a way of estimating inlier scale. Our experiments show that without prior knowledge of inlier ratio, inlier scale and the number of structures, our method generates reliable and consistent hypotheses efficiently.

REFERENCES FOR SECTION 1 THROUGH SECTION 5 ABOVE

1. Chinneck, J. W.: Feasibility and Infeasibility in Optimization: Algorithms and Computational Methods, 1st edition, Springer, Heidelberg 2007.
2. Li, H.: Consensus Set Maximization with guaranteed global optimality for robust geometry estimation. In ICCV 2009.
3. Fischler, M. A., Bolles, R. C.: RANSAC: A paradigm for model fitting with applications to image analysis and automated cartography. Comm. of the ACM 24 1981: 381-395
4. Chum, O., Matas, J., Kittler, J.: Locally optimized RANSAC. In: DAGM 2003.
5. Kanazawa, Y., Kawakami, H.: Detection of planar regions with uncalibrated stereo using distributions of feature points. In: BMVC 2004.
6. Ni, K., Jin, H., Dellaert, F.: GroupSAC: Efficient consensus in the presence of groupings. In ICCV. 2009.
7. Sattler, T., Leibe, B., Kobbelt, L.: SCRAMSAC: Improving RANSAC's efficiency with a spatial consistency filter. In: ICCV 2009.
8. Tordo, B. J., Murray, D. W.: Guided-MLESAC: Faster image transform estimation by using matching priors. IEEE Trans. Pattern Anal. Mach. Intell. (27) 2005:1523-1535
9. Chum, O., Matas, J.: Matching with PROSAC—progressive sample consensus. In CVPR. 2005.
10. D. R. Myatt, Philip H. S. Torr, Slawomir J. Nasuto, J. Mark Bishop, R. Craddock.: NAPSAC: High Noise, High Dimensional Robust Estimation—it's in the Bag. In BMVC 2002.
11. Tat-Jun Chin, Jin Yu, David Suter: Accelerated Hypothesis Generation for Multistructure Data via Preference Analysis. IEEE Trans. Pattern Anal. Mach. Intell. 34(4): 2012 625-638
12. Hoi Sim Wong, Tat-Jun Chin, Jin Yu, David Suter: Dynamic and hierarchical multi-structure geometric model fitting. In ICCV 2011: 1044-1051
13. T.-J. Chin, J. Yu, and D. Suter. Accelerated hypothesis generation for multi-structure robust fitting. In ECCV 2010.
14. Hoi Sim Wong, Tat-Jun Chin, Jin Yu, David Suter: Efficient Multi-structure Robust Fitting with Incremental Top-k Lists Comparison. In ACCV 2010: 553-564.
15. Trung-Thanh Pham, Tat-Jun Chin, Jin Yu, David Suter: The Random Cluster Model for robust geometric fitting. CVPR 2012: 710-717
16. Toldo, R., A. Fusiello.: Robust Multiple Structures Estimation with JLinkage. In ECCV 2008: 537-547.

17. Chin, T.-J., H. Wang, D. Suter.: Robust Fitting of Multiple Structures: The Statistical Learning Approach. In ICCV 2009: 413-420.
18. Zhang, W., J. Kosecka.: Nonparametric Estimation of Multiple Structures with Outliers. LNCS, DVW 2006: 4358. 60-74.
19. Zuliani, M., Kenney, C., Manjunath, B.: The multiransac algorithm and its application to detect planar homographies. In ICIP 2005: Volume 3.
20. A. Delong, A. Osokin, H. Isack, and Y. Boykov.: Fast approximate energy minimization with label costs. In CVPR, 2010.
21. H. Wang and D. Suter.: Robust adaptive-scale parametric model estimation for computer vision. IEEE Trans. PAMI, 26(11):1459-1474, November 2004.
22. J. Choi and G. Medioni.: StaRSaC: Stable random sample consensus for parameter estimation. CVPR, 2009.
23. Rahul Raguram, Jan-Michael Frahm: RECON: Scale-adaptive robust estimation via Residual Consensus. ICCV 2011: 1299-1306
24. Hanzi Wang, Tat-Jun Chin, David Suter: Simultaneously Fitting and Segmenting Multiple-Structure Data with Outliers. IEEE Trans. Pattern Anal. Mach. Intell. 34(6): 1177-1192 (2012)
25. Enqvist, O., Kahl, F.: Two view geometry estimation with outliers. In BMVC 2009.
26. C. Yu, Y. Seo, and S. Lee.: Photometric stereo from maximum feasible lambertian reflec-tions. In ECCV, 2010.
27. R. Hartley and F. Kahl. Global Optimization through Rotation Space Search. IJCV, 82(1):64-79, 2009.
28. F. Kahl. Multiple view geometry and the L-infinity norm. In ICCV 2005: 1002-1009.
29. R. Hartley and A. Zisserman.: Multiple view geometry in computer vision 2nd ed. Cambridge University Press, 2004.
30. Gurobi optimization. http://www.gurobi.com/, 2010
31. http://www.robots.ox.ac.uk/~vgg/data/
32. http://www.csse.uwa.edu.au/~pk/research/matlabfns/
33. http://cs.adelaide.edu.au/~tjchin/doku.php
34. http://cs.adelaid.edu.au/~hwong/doku.php?id=data
35. http://cs.adelaide.edu.au/~dsuter/code and data
36. http://www.vision.jhu.edu/data/hopkins155/
37. http://cs.adelaide.edu.au/~trung/home.php It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.
While one or more exemplary embodiments have been described with reference to the figures, it will be understood by those of ordinary skill in the art that various changes in form and details may be made therein without departing from the spirit and scope as defined by the following claims.

What is claimed is:
1. An image processing apparatus comprising:
   a storage configured for storing image data comprising data of a first model; and
   a processor configured for determining a final model parameter set and a final inlier scale of the first model by iteratively performing a model estimation process and an inlier scale estimation process, wherein
      the model estimation process determines a model parameter set from the image data by using an initial inlier scale, and
      the inlier scale estimation process determines an inlier scale by using the model parameter set,
   wherein when the model estimation process is repeated, and in the repeated model estimation process, a new model parameter set is determined by using a previously determined inlier scale which was determined during an immediately previously determined inlier scale estimation process,
   wherein in the inlier scale estimation process, a new inlier scale is determined using a model parameter set determined according to an immediately previously performed model estimation process,
   wherein the image data comprises data of multiple models including the first model and a second model,
   wherein the processor is further configured for:
      performing an inlier removal process whereby first inlier data indicating inliers located within the final inlier scale of the first model is removed from the image data based on the final model parameter set and the final inlier scale of the first model, and
      performing a final determination process whereby a final model parameter set and a final inlier scale of the second model are determined by iteratively performing the model estimation process and the inlier scale estimation process on the image data from which the first inlier data has been removed,
   wherein the model estimation process is performed using Maximum Feasible Subsystem (MaxFS) as a deterministic method, and
   wherein the inlier scale estimation process is performed using Iterative Kth Ordered Scale Estimator (IKOSE).
2. The apparatus of claim 1, wherein model parameter sets and inlier scales determined by iteratively performing the model estimation process and the inlier scale estimation process converge to the final model parameter set and the final inlier scale of the first model, respectively.
3. The apparatus of claim 1, wherein the processor determines final model parameter sets and final inlier scales of all of the multiple models by iteratively performing, each time a final model parameter set and a final inlier scale of one of the multiple models are determined, the inlier removal process and the final determination process on another one of the multiple models.
4. The apparatus of claim 1, wherein the initial inlier scale is set by a user input.
5. The apparatus of claim 1,
   wherein the image data comprises an ultrasound image, and
   wherein the first model is a geometric shape, and is one of a straight line, a circle, an ellipse, a plane, a sphere, and a curved surface.
6. The apparatus of claim 1, wherein the first model is a linear or non-linear model that is estimated from the image data and is at least one from among homography estimation, fundamental matrix estimation, optical flow estimation, and motion estimation.
7. An image processing method comprising:
   iteratively performing a model estimation process and an inlier scale estimation process on image data including data of a first model, wherein the model estimation process determines a model parameter set from the image data by using an initial inlier scale, and the inlier scale estimation process determines an inlier scale by using the model parameter set, and
   determining a final model parameter set and a final inlier scale of the first model based on a result obtained by the iteratively performing of the model estimation process and the inlier scale estimation process, wherein when the model estimation process is repeated, and in the repeated model estimation process, a new model parameter set is determined by using a previously determined inlier scale which was determined during an immediately previously determined inlier scale estimation process, wherein in the inlier scale estimation process, a new inlier scale is determined using a model parameter set determined according to an immediately previously performed model estimation process, when the image data comprises data of multiple models including the first model and a second model, the method further comprising:

performing an inlier removal process whereby first inlier data indicating inliers located within the final inlier scale of the first model is removed from the image data based on the final model parameter set and the final inlier scale of the first model; and performing a final determination process whereby a final model parameter set and a final inlier scale of the second model are determined by iteratively performing the model estimation process and the inlier scale estimation process on the image data from which the first inlier data has been removed, wherein the model estimation process is performed using Maximum Feasible Subsystem (MaxFS) as a deterministic method, and wherein the inlier scale estimation process is performed using Iterative Kth Ordered Scale Estimator (IKOSE).

8. The method of claim 7, wherein model parameter sets and inlier scales determined by iteratively performing the model estimation process and the inlier scale estimation process converge to the final model parameter set and the final inlier scale of the first model, respectively.

9. The method of claim 7, wherein final model parameter sets and final inlier scales of all of the multiple models are determined by iteratively performing, each time a final model parameter set and a final inlier scale of one of the multiple models are determined, the inlier removal process and the final determination process on another one of the multiple models.

10. The method of claim 7, wherein the initial inlier scale is set by a user input.

11. The method of claim 7, wherein the image data comprises an ultrasound image, and wherein the first model is a geometric shape, and is one of a straight line, a circle, an ellipse, a plane, a sphere, and a curved surface.

12. The method of claim 7, wherein the first model is a linear or non-linear model that is estimated from the image data and is at least one from among homography estimation, fundamental matrix estimation, optical flow estimation, and motion estimation.

13. A non-transitory computer-readable recording medium having recorded thereon a program for executing the method of claim 7 on a computer.

* * * * *